(12) United States Patent
Stinchcomb et al.

(10) Patent No.: US 9,011,874 B2
(45) Date of Patent: *Apr. 21, 2015

(54) COMPOSITIONS, METHODS AND USES FOR POXVIRUS ELEMENTS IN VACCINE CONSTRUCTS

(75) Inventors: Dan T. Stinchcomb, Fort Collins, CO (US); Jorge E. Osorio, Mount Horeb, WI (US); Timothy D. Powell, Fort Collins, CO (US); Jeremy Jones, Memphis, TN (US)

(73) Assignee: Takeda Vaccines, Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/510,601

(22) PCT Filed: Nov. 22, 2010

(86) PCT No.: PCT/US2010/057682
§ 371 (c)(1),
(2), (4) Date: Oct. 29, 2012

(87) PCT Pub. No.: WO2011/063359
PCT Pub. Date: May 26, 2011

(65) Prior Publication Data
US 2013/0136767 A1    May 30, 2013

Related U.S. Application Data

(60) Provisional application No. 61/263,327, filed on Nov. 20, 2009.

(51) Int. Cl.
| | | |
|---|---|---|
| *A61K 49/00* | (2006.01) |
| *A61K 39/38* | (2006.01) |
| *A61K 39/295* | (2006.01) |
| *A61K 39/145* | (2006.01) |
| *A61K 39/245* | (2006.01) |
| *C12Q 1/70* | (2006.01) |
| *C12N 15/863* | (2006.01) |
| *A61K 39/12* | (2006.01) |
| *A61K 39/00* | (2006.01) |
| *C07K 14/005* | (2006.01) |

(52) U.S. Cl.
CPC .............. *C12N 15/863* (2013.01); *A61K 39/12* (2013.01); *A61K 39/00* (2013.01); *A61K 39/145* (2013.01); *C07K 14/005* (2013.01); *A61K 2039/5256* (2013.01); *C12N 2760/16034* (2013.01); *C12N 2760/16134* (2013.01); *C07K 2319/02* (2013.01); *C12N 2710/24143* (2013.01); *C12N 2760/16122* (2013.01)

(58) Field of Classification Search
None
See application file for complete search history.

(56) References Cited

FOREIGN PATENT DOCUMENTS

| WO | WO 97/02355 A1 | 1/1997 |
| WO | WO 01/68820 A1 | 9/2001 |
| WO | WO 2008/061939 A1 | 5/2008 |

OTHER PUBLICATIONS

Patel et al., The N-terminal 22 amino acids encoded by the gene specifying the major secreted protein of vaccinia virus, strain Lister, can function as a signal sequence to direct the export of a foreign protein, 1992, Virus Research, vol. 26, No. 3, pp. 197-212.*
Kreijtz et al., MVA-Based H5N1 Vaccine Affords Cross-Clade Protection in Mice against Influenza A/H5N1 Viruses at Low Doses and after Single Immunization, 2009, PLoS one, vol. 4, No. 11, pp. 1-8.*
GenBank Accession P21044, RecName: Full=Protein C13 [Vaccinia virus Copenhagen], Apr. 3, 2013.*
Brewoo Joseph H et al: "Efficacy and safety of a modified vaccinia Ankara (MVA) vectored plague vaccine in mice", Vaccine vol. 28, No. 36, Aug. 2010, pp. 5891-5899, XPOO2718191, ISSN: 0264-410X.
Blanchard et al., Modified vaccinia virus Ankara undergoes limited replication in human cells and lacks several immunomodulatory proteins: implications for use as a human vaccine. Journal of General Virology, 1998, vol. 79, pp. 1159-1167.

* cited by examiner

*Primary Examiner* — Benjamin P Blumel
(74) *Attorney, Agent, or Firm* — Faegre Baker Daniels LLP

(57) ABSTRACT

Embodiments of the present invention generally disclose methods, compositions and uses for generating and expressing poxvirus constructs. In some embodiments, constructs may contain an influenza virus gene segment. In certain embodiments, methods generally relate to making and using compositions of constructs including, but not limited to, poxvirus vaccine compositions. In other embodiments, vaccine compositions are reported of use in a subject.

19 Claims, 24 Drawing Sheets

Table 1: MVA influenza transfer vectors and MVA constructs.

| Transfer Vector designation | Sel | IRES | Secretory signal tP78484A | C13L | B8R | Flu, HA | Flu, HA native | flu, HAt | flu, Hat nat | Flu, NA | Flu, NP | Flu, NA trunc | Recombinant construct |
|---|---|---|---|---|---|---|---|---|---|---|---|---|---|
| pl52 | X |   |   |   |   |   | X |   |   |   |   |   | MVA/52-1B1A |
| pl53 | X | X | X |   |   | X |   |   |   |   |   |   | MVA/53-3A1A |
| pl54 | X |   | X |   |   | X |   |   |   |   |   |   | MVA/54-1A1A |
| pl69 | X |   |   | X |   | X |   |   |   |   |   |   | MVA/69-1A1A |
| pl70 | X |   |   |   | X | X |   |   |   |   |   |   | MVA/70-1A1A |
| pl71 | X | X |   | X |   | X |   |   |   |   |   |   | MVA/71-1A1A |
| pl72 | X | X |   |   | X | X |   |   |   |   |   |   | MVA/72-1A1A |
| pl73 | X |   |   |   |   |   |   |   | X |   |   |   | MVA/73-1A1A |
| pl74 | X |   | X |   |   |   |   | X |   |   |   |   | MVA/74-1A1A |
| pl75 | X |   |   | X |   |   |   | X |   |   |   |   | MVA/75-1A1A |
| pl76 | X |   |   |   | X |   |   | X |   |   |   |   | MVA/76-1A1A |
| pl77 | X | X | X |   |   |   |   | X |   |   |   |   | MVA/77-1A1A |
| pl78 | X | X |   | X |   |   |   | X |   |   |   |   | MVA/78-1A1A |
| pl79 | X | X |   |   | X |   |   | X |   |   |   |   | MVA/79-1A1A |
| pl80 | X |   |   |   |   |   |   |   |   |   | X |   | MVA/80-2A1A |
| pl81 | X |   |   |   |   |   |   |   |   | X |   |   | MVA/81-1A1A |
| pl83 | X |   | X |   |   |   |   |   |   | X |   |   | MVA/83-1A1A |
| pl84 | X |   |   | X |   |   |   |   |   | X |   |   | MVA/84-1A1A |
| pl85 | X |   |   |   | X |   |   |   |   | X |   |   | MVA/85-1A1A |
| pl86 | X | X | X |   |   |   |   |   |   | X |   |   | MVA/86-1A1A |
| pl87 | X | X |   | X |   |   |   |   |   | X |   |   | MVA/87-1A1A |
| pl88 | X | X |   |   | X |   |   |   |   | X |   |   | MVA/88-1A1A |
| pl89 | X |   | X |   |   |   |   |   |   |   | X |   | MVA/89-2A1A |
| pl90 | X |   |   | X |   |   |   |   |   |   | X |   | MVA/90-1A1A |
| pl91 | X |   |   |   | X |   |   |   |   |   | X |   | MVA/91-1A1A |
| pl92 | X | X | X |   |   |   |   |   |   |   | X |   | MVA/92-1A1A |
| pl93 | X | X |   | X |   |   |   |   |   |   | X |   | MVA/93-1A1A |
| pl94 | X | X |   |   | X |   |   |   |   |   | X |   | MVA/84-1A1A |
| pl95 | X |   |   | X |   |   |   |   |   |   |   | X | MVA/95-1A1A |
| pl96 | X | X |   | X |   |   |   |   |   |   |   | X | MVA/96-1A1A |

Fig. 12A

MVA/IRES/tpa/HAt

Fig. 12B

MVA/IRES/C13L/HAt

Fig. 14A

MVA/IRES/tpa/HA Native

Fig. 14B

MVA/IRES/C13L/HA Native

Fig. 15A

MVA/IRES/tpa/HAt

MVA/IRES/C13L/HAt

Series1
Series2
Series3

MVA/IRES/C13L/HAt

Fig. 20

SEQUENCE LISTING

```
<160> NUMBER OF SEQ ID NOS: 10

<210> SEQ ID NO 1
<211> LENGTH: 18
<212> TYPE: PRT
<213> ORGANISM: Artificial Sequence
<220> FEATURE:
<223> OTHER INFORMATION: vaccinia virus secretory signal

<400> SEQUENCE: 1

Met Met Ile Tyr Gly Leu Ile Ala Cys Leu Ile Phe Val Thr Ser Ser
1               5                   10                  15

Ile Ala
```

<210> SEQ ID NO 2
<211> LENGTH: 17
<212> TYPE: PRT
<213> ORGANISM: Artificial Sequence
<220> FEATURE:
<223> OTHER INFORMATION: vaccinia virus secretory signal

<400> SEQUENCE: 2

Met Arg Tyr Ile Ile Ile Leu Ala Val Leu Phe Ile Asn Ser Ile His
1               5                   10                  15

Ala

<210> SEQ ID NO 3
<211> LENGTH: 32
<212> TYPE: DNA
<213> ORGANISM: Artificial Sequence
<220> FEATURE:
<223> OTHER INFORMATION: primer

<400> SEQUENCE: 3
tcgtcccggg ttattttcca ccatattgcc gt                                   32

<210> SEQ ID NO 4
<211> LENGTH: 94
<212> TYPE: DNA
<213> ORGANISM: Artificial Sequence
<220> FEATURE:
<223> OTHER INFORMATION: primer

<400> SEQUENCE: 4
tcgtgccggc tggactagcg atggatgaag tcacgaatat aagacacgct attaatccgt     60
atatcatcat attatcatcg tgttttcaa agga                                  94

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
tcgtcccggg ttattttcca ccatattgcc gt                                   32

<210> SEQ ID NO 6
<211> LENGTH: 88
<212> TYPE: DNA
<213> ORGANISM: Artificial Sequence
<220> FEATURE:
<223> OTHER INFORMATION: primer

<400> SEQUENCE: 6
tcgtgccggc tttagcgtgt atactattaa tgaacaaaac tgcgagaatt ataatatatc     60
tcatattatc atcgtgtttt tcaaagga                                        88

<210> SEQ ID NO 7
<211> LENGTH: 72
<212> TYPE: DNA
<213> ORGANISM: Artificial Sequence
<220> FEATURE:
<223> OTHER INFORMATION: primer

<400> SEQUENCE: 7
ccgggatgat gatatacgga ttaatagcgt gtcttatatt cgtgacttca tccatcgcta     60

```
gtccagccgg cg                                                           72

<210> SEQ ID NO 8
<211> LENGTH: 72
<212> TYPE: DNA
<213> ORGANISM: Artificial Sequence
<220> FEATURE:
<223> OTHER INFORMATION: primer

<400> SEQUENCE: 8
ctagcgccgg ctggactagc gatggatgaa gtcacgaata taagacacgc tattaatccg      60
tatatcatca tc                                                           72

<210> SEQ ID NO 9
<211> LENGTH: 66
<212> TYPE: DNA
<213> ORGANISM: Artificial Sequence
<220> FEATURE:
<223> OTHER INFORMATION: primer

<400> SEQUENCE: 9
ccgggatgag atatattata attctcgcag ttttgttcat taatagtata cacgctaaag      60
ccggcg                                                                  66

<210> SEQ ID NO 10
<211> LENGTH: 66
<212> TYPE: DNA
<213> ORGANISM: Artificial Sequence
<220> FEATURE:
<223> OTHER INFORMATION: primer

<400> SEQUENCE: 10
ctagcgccgg ctttagcgtg tatactatta atgaacaaaa ctgcgagaat tataatatat      60
ctcatc                                                                  66
```

COMPOSITIONS, METHODS AND USES FOR POXVIRUS ELEMENTS IN VACCINE CONSTRUCTS

CROSS REFERENCE TO RELATED APPLICATION

This PCT application claims the benefit of U.S. Provisional Patent Application Ser. No. 61/263,327, filed on Nov. 20, 2009. Pursuant to 35 U.S.C. 119(e), the prior application is incorporated herein by reference in its entirety for all purposes.

FEDERALLY FUNDED RESEARCH

This invention was made in part with government support under Grant Nos. 1R41AI074308-01 and 5R41AI074308-02 awarded by The National Institutes of Health. The government has certain rights in the invention.

FIELD

Embodiments of the present invention report methods, compositions and uses for generating vaccine compositions. In some embodiments, poxvirus elements can be used in viral constructs, for example, a construct of use in vaccines. In some embodiments, a poxvirus element may be a secretory signal. In certain embodiments, methods for making and using constructs for vaccine preparations that include, but are not limited to, using attenuated or modified vaccinia virus vectors that can express peptides derived from different organisms. In other embodiments, constructs may be generated for use in vaccination against influenza. In yet other embodiments, compositions and methods herein report pre-exposing a subject to a construct composition prior to administering a vaccine to the subject.

BACKGROUND

Vaccines to protect against viral infections have been effectively used to reduce the incidence of human disease. One of the most successful technologies for viral vaccines is to immunize animals or humans with a weakened or attenuated strain of the virus (a "live, attenuated virus"). Due to limited replication after immunization, the attenuated strain does not cause disease. However, the limited viral replication is sufficient to express the full repertoire of viral antigens and generates potent and long-lasting immune responses to the virus. Thus, upon subsequent exposure to a pathogenic strain of the virus, the immunized individual is protected from disease. These live, attenuated viral vaccines are amongst the most successful vaccines used in public health.

Influenza is an orthomyxovirus with three genera, types A, B, and C. The types are distinguished by the nucleoprotein antigenicity. Influenza B is a human virus and does not appear to be present in an animal reservoir. Type A viruses exist in both human and animal populations, with significant avian and swine reservoirs.

Annual influenza A virus infections have a significant impact in terms of human lives, between 500,000 and 1,000,000 die worldwide each year, and economic impact resulting from direct and indirect loss of productivity during infection. Of even greater concern is the ability of influenza A viruses to undergo natural and engineered genetic change that could result in the appearance of a virus capable of rapid and lethal spread within the population.

One of the most dramatic events in influenza history was the so-called "Spanish Flu" pandemic of 1918-1919. In less than a year, between 20 and 40 million people died from influenza, with an estimated one fifth of the world's population infected. The US military was devastated by the virus near the end of World War I, with 80% of US army deaths between 1918 and 1919 due to influenza infection. Because it is a readily transmitted, primarily airborne pathogen, and because the potential exists for the virus to be genetically engineered into novel forms, influenza A represents a serious biodefense concern.

Current public and scientific concern over the possible emergence of a pandemic strain of influenza, poxviruses or other pathogenic or non-pathogenic viruses requires effective preventative measures.

SUMMARY

Embodiments of the present invention report methods, compositions and uses for generating novel vaccine compositions. In some embodiments, poxvirus elements can be used in vaccine constructs. In other embodiments, compositions and methods for administering poxvirus elements prior to receiving a vaccine can be used, for example, to circumvent interference from pre-exposure to poxvirus elements. In some embodiments, a poxvirus element may be a secretory signal or other poxvirus element. In certain embodiments, methods for making and using constructs for vaccine preparations including, but not limited to, using attenuated or modified vaccinia virus vectors expressing viral-bacterial, protozoal, fungal, or mammalian peptides to induce an immune response in a subject. In other embodiments, constructs may be generated for use in vaccines that protect against infectious diseases or in vaccines used as therapies (e.g. for cancer, diabetes, Alzheimer's disease, etc.). Some embodiments are of use as a therapeutic or as a prophylactic against a medical condition in a subject. In other embodiments, constructs may be generated for use in vaccination against viral diseases. In further embodiments, constructs may be generated for use in vaccines to protect from influenza.

Embodiments of the present invention generally relate to methods, compositions and uses for expressing peptides (e.g. poxvirus associated peptides and non-poxvirus peptides) to stimulate immune responses. In some embodiments, viral peptide formulations presented herein can be used to boost an immune response in a subject before, during and/or after vaccination of the subject or to overcome pre-existing immunity (e.g. previous poxvirus exposure) in the subject. Certain embodiments report making and using constructs of the present invention for treating or protecting a subject having been exposed or likely to be exposed to a pathogen. In accordance with these embodiments a pathogen can include a bacterial, viral, protozoal or fungal pathogen. In some embodiments, a pathogen can be influenza virus.

In accordance with embodiments disclosed herein, constructs may include, but are not limited to, attenuated or modified vaccinia virus vectors expressing bacterial-, viral-, fungal-, protozoal-associated gene segments (e.g. non-poxvirus peptides). For example, certain methods and compositions report making and using compositions having constructs including, but not limited to, attenuated or modified vaccinia virus vectors expressing influenza-associated gene segments in order to induce an immune response in a subject against the influenza. Certain compositions report constructs having antigens or peptides derived from influenza and associated with or combined with poxviruses related elements. Influenza gene or gene segments can include, but are not limited to, hemagglutinin (HA gene segment), neuraminidase (NA gene segment), nucleoprotein (NP gene segment), matrix protein (M gene segment), polymerase (P) and a combination thereof. Some embodiments report vaccine compositions capable of reducing or preventing infection in a subject caused by exposure to a poxvirus and/or influenza virus. Some embodiments concern using a fragment of one or more influenza gene segments for example, a fragment can include at least 6, or at least 8, or at least 10, or at least 15, or at least 20 contiguous etc amino acids of an influenza gene segment, up to the full length of the gene segment.

In some aspects, constructs of use as vaccine compositions, can include a secretory signal sequence alone or in combination with a translation control region sequence. In accordance with these embodiments, the secretory signal sequence can be one or more signal sequences from a poxvirus. In other embodiments, the secretory signal sequence can include, but are not limited to, tissue plasminogen activator (tPA) leader sequence, the co-factor leader sequence, the pre-proinsulin leader sequence, the invertase leader sequence, the immunoglobulin A leader sequence, the ovalbumin leader sequence, and the P-globin leader sequence or other proleader sequences and combinations thereof.

In certain embodiments, a pre-boost of a construct may be used to induce a greater immune response in a subject to a subsequent vaccination. In some embodiments, a vaccinia virus derived gene sequence may be used to pre-boost a subject. In accordance with these embodiments, a pre-boost construct can contain modified vaccinia Ankara (MVA). It is contemplated that these pre-boosts can be administered to a subject by any method. For example, the pre-boost can be introduced intramuscularly or intradermally or by another method. In addition, a pre-boost may be administered to a subject followed by introduction of a construct having one or more elements derived from a pathogen or associated with a condition to boost an immune response in the subject. In certain examples, a pre-boost could be 6 months or less prior to a vaccination, or 5 months or less, or 4 months or less, or 3 months or less, or 1 month or less or a few weeks or immediately prior to administering a vaccine to a subject. Administration regimens are readily determinable by one skilled in the art for pre-boosts, boost and post-boosts related to vaccinating a subject against an infection or a condition.

Other embodiments concern kits for making or using compositions disclosed. It is reported that a kit may include constructs having a modified vaccinia viral vector and one or more enterobacterial antigen.

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

Figure 1A:
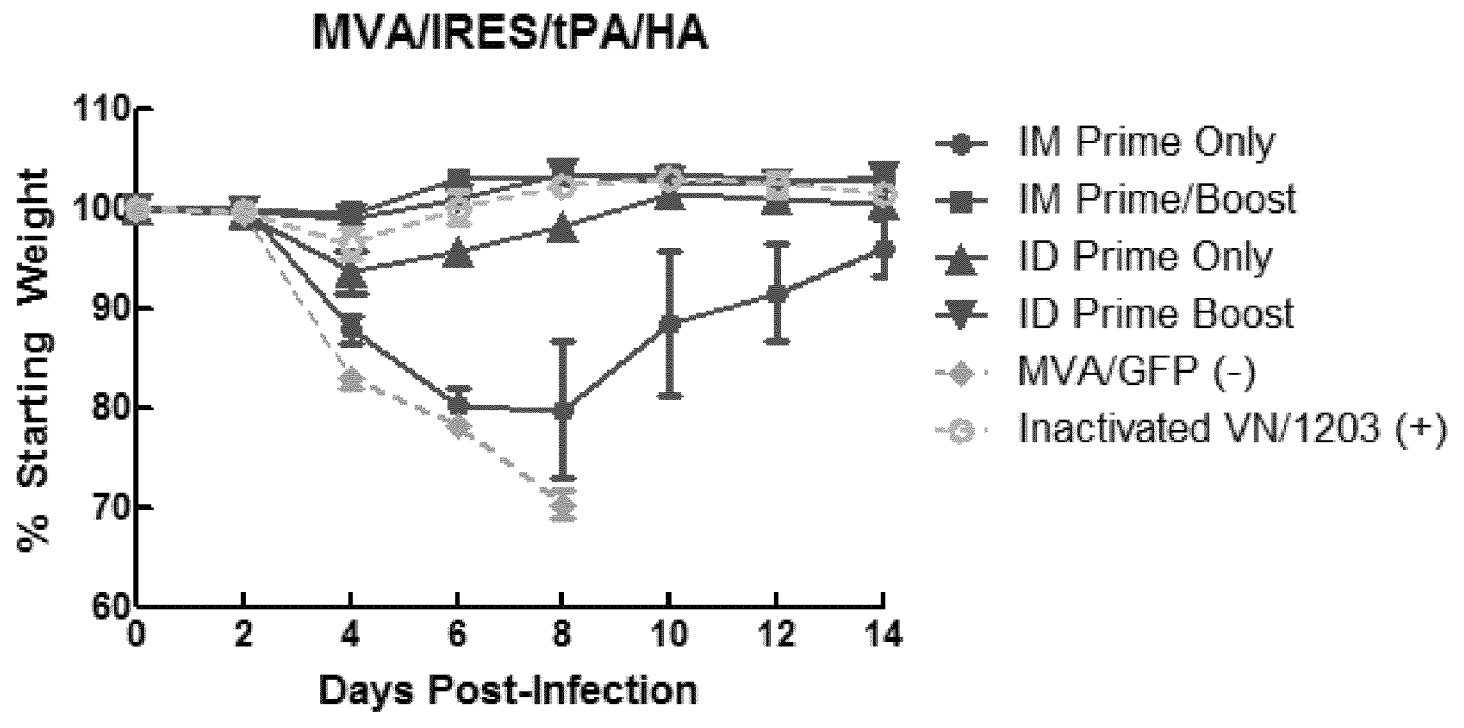

FIGS. 1A and 1B represent exemplary plots of parameters in mice after intramuscular (IM) or intradermal (ID) introduction of various constructs of some embodiments described herein to the mice followed by challenge with influenza, FIG. 1A) Weight loss and FIG. 1B) Viral Lung titers on day 4 post-challenge.

FIGS. 2A-2C represent exemplary plots of experiments where mice were vaccinated intradermal (ID) with various influenza challenge concentration and then examined on day 63 post-vaccination. Weight loss curves are displayed for some of the constructs FIG. 2A) MVA/IRES/tPA/HA, FIG. 2B) MVA/IRES/C13L/HA, and FIG. 2C) MVA/HA native.

FIG. 3 represents an exemplary plot that illustrates various constructs and effects on long-term immune protection in mice against a viral insult.

FIG. 4 represents an exemplary plot that illustrates cross-clade protection using various viral-derived antigens.

FIG. 5 represents an exemplary plot of mice tested with certain constructs described herein, described herein to the mice followed by a viral challenge.

FIGS. 6A and 6B represent exemplary plots of parameters in mice after intramuscular (IM) introduction of various constructs of some embodiments described herein to the mice followed by challenge with influenza, FIG. 6A) Weight loss and FIG. 6B) Survival post-challenge.

FIGS. 7A and 7B represent exemplary plots of parameters in mice after intradermal (ID) introduction of various constructs of some embodiments described herein to the mice followed by challenge with influenza, FIG. 7A) Weight loss and FIG. 7B) Survival post-challenge.

FIGS. 8A and 8B represent exemplary plots of parameters in mice after (FIG. 8A) intramuscular (IM) or (FIG. 8B) intradermal (ID) introduction of various constructs of some embodiments described herein to the mice followed by challenge with influenza.

FIG. 9 represents an exemplary plot that illustrates viral titers in lung after introduction of various constructs of some embodiments described herein to the mice followed by challenge with influenza.

FIGS. 10A and 10B represent exemplary plots of percent weight change in mice after introduction of 2 different constructs of some embodiments described herein having the HA gene segment in each construct followed by challenge with influenza. FIG. 10A represents construct MVA/HA and FIG. 10B represents construct MVA/IRES/tpa/HA.

FIG. 10C illustrates Table 1 which represents MVA influenza transfer vectors and constructs.

FIGS. 11A and 11B represent exemplary plots of percent weight change in mice after introduction of 2 different constructs of some embodiments described herein followed by challenge with influenza. FIG. 11A represents construct MVA/IRES/C13L/HA and FIG. 11B represents construct MVA-GFP.

Figures 12A, 12B:
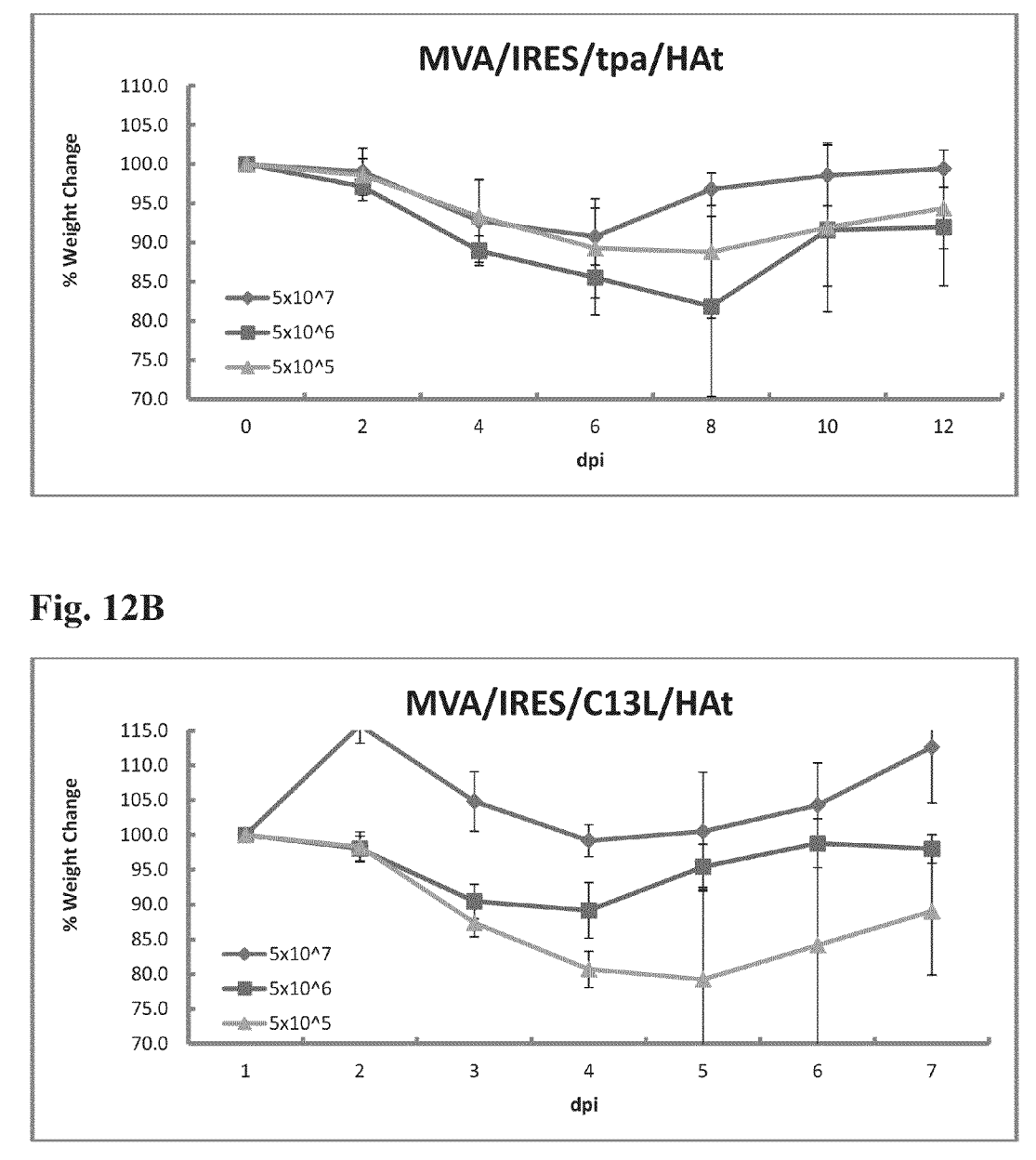

FIGS. 12A and 12B represent exemplary plots of percent weight change in mice after introduction of 2 different constructs at various concentrations of some embodiments described herein followed by challenge with influenza. FIG. 12A represents construct MVA/IRES/tpa/HAt and FIG. 12B represents construct MVA/IRES/C13L/HAt.

FIGS. 13A and 13B represent exemplary plots of survival in mice after introduction of 2 different constructs at various concentrations of some embodiments described herein followed by challenge with influenza. FIG. 13A represents construct MVA/HA and FIG. 13B represents construct MVA/IRES/tpa/HA.

Figures 14A, 14B:
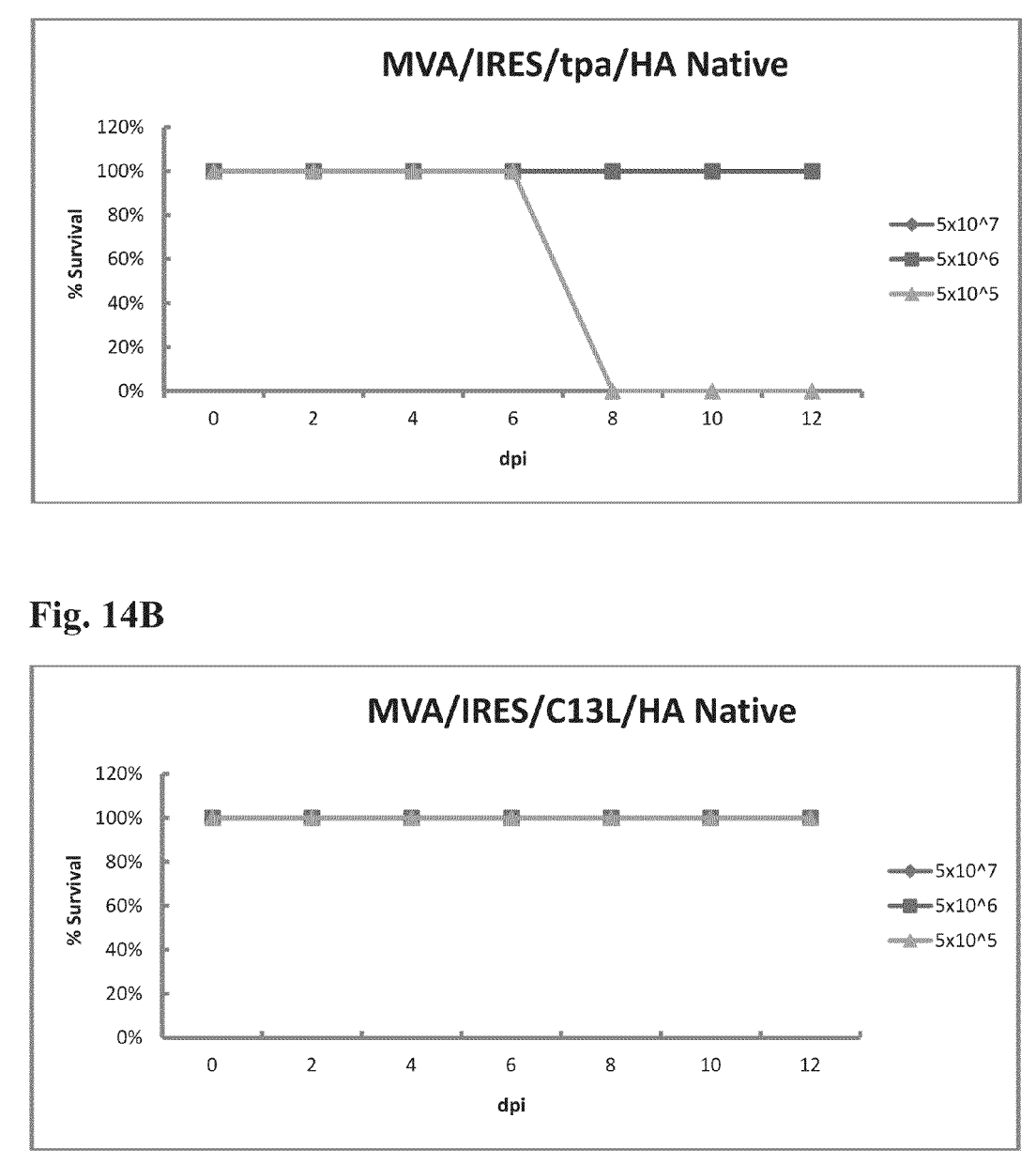

FIGS. 14A and 14B represent exemplary plots of survival in mice after introduction of 2 different constructs at various concentrations of some embodiments described herein followed by challenge with influenza. FIG. 14A represents construct MVA/IRES/tpa/HA and FIG. 14B represents construct MVA/IRES/C13L/HA.

FIGS. 15A and 15B represent exemplary plots of survival in mice after introduction of 2 different constructs at various concentrations of some embodiments described herein followed by challenge with influenza (dpi represents days post infection). FIG. 15A represents construct MVA/IRES/tpa/HAt and FIG. 15B represents construct MVA/IRES/C13L/HAt.

FIG. 16A represents construct MVA/HA and FIG. 16B represents construct MVA/IRES/tpa/HA.

FIGS. 17A and 17B represent exemplary plots of clinical scores (e.g. physical and physiological parameters) in mice after introduction of 2 different constructs at various concentrations of some embodiments described herein followed by challenge with influenza. FIG. 17A represents construct MVA/IRES/C13L/HA and FIG. 17B represents construct MVA/IRES/tpa/HAt.

FIG. 18 represents an exemplary plot of clinical scores (e.g. physical and physiological parameters) in mice after introduction of a construct at various concentrations of some embodiments described herein followed by challenge with influenza.

FIG. 20 represents an exemplary plot of survival of mice challenged above after exposure to the same constructs as in FIGS. 19A and 19B.

DEFINITIONS

Figure 1B:
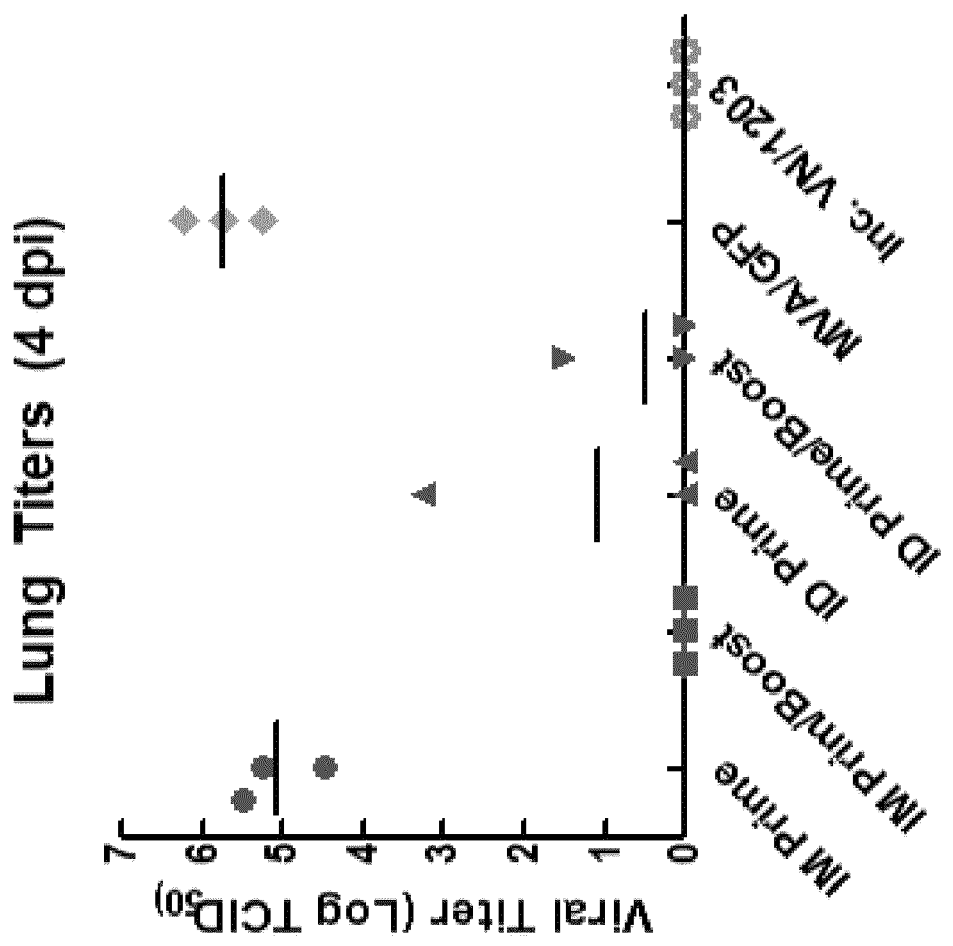

As used herein, "a" or "an" can mean one or more than one of an item.

As used herein the specification, "subject" or "subjects" can include, but are not limited to, mammals such as humans or mammals, domesticated or wild, for example dogs, cats, other household pets (e.g. hamster, guinea pig, mouse, rat), ferrets, rabbits, pigs, horses, cattle, prairie dogs, wild rodents, or zoo animals. A subject can be an adult or a child.

As used herein, "about" can mean plus or minus ten percent.

As used herein, "attenuated virus" can mean a virus that demonstrates reduced or no clinical signs of disease when administered to a subject such as a mammal (e.g. human or an animal).

As used herein, "MSC" can mean multiple cloning site.

As used herein, "dSP" can mean divergent vaccinia promoter.

As used herein, "MVA" can mean modified vaccinia Ankara.

As used herein, "EMCV" can mean encephalomyocarditis virus.

As used herein, "IRES" can mean internal ribosome entry site from encephalomyocarditis virus or other viruses.

As used herein, "IRES(A7)" can mean IRES from encephalomyocarditis virus with 7 adenosine residues in bifurcation loop; source-pCITE-1.

As used herein, "IRES(A6)" can mean IRES from encephalomyocarditis virus mutated to have 6 adenosine residues in bifurcation loop.

As used herein, "pDIIIgfp" can mean MVA del III gfp marker transfer plasmid.

As used herein, "pI*" can mean transfer vector plasmids.

As used herein, "tPA" can mean secretory signal from tissue plaminogen activator.

As used herein, "se/1" can mean synthetic optimized early late poxvirus promoter.

As used herein, "H6" can mean the vaccinia gene H6 early/late native poxvirus promoter.

As used herein, "del III" can mean modified vaccinia Ankara deletion region III.

As used herein, "GFP" can mean enhanced green fluorescent protein.

As used herein, "CEF" can mean chicken embryo fibroblasts.

As used herein, "RCN" can mean raccoon pox virus.

Description

In the following sections, various exemplary compositions and methods are described in order to detail various embodiments. It will be obvious to one skilled in the art that practicing the various embodiments does not require the employment of all or even some of the details outlined herein, but rather that concentrations, times and other details may be modified through routine experimentation. In some cases, well-known methods or components have not been included in the description.

Embodiments of the present invention concern methods, compositions and uses for generating novel vaccine compositions. In some embodiments, poxvirus elements can be used in vaccine constructs or in pre-immunization constructs for introduction to a subject. In certain embodiments, poxvirus elements can be used to pre-immunize a subject prior to receiving a vaccine. In some embodiments, a poxvirus element can be a secretory signal or other poxvirus element. Other embodiments concern methods for making and using constructs including, but not limited to, attenuated or modified vaccinia virus vectors expressing viral, bacterial, protozoal fungal, or mammalian derived peptides. In other embodiments, constructs may be generated for use in vaccines that protect against infectious diseases or in vaccines used as therapies (e.g. for cancer, diabetes, Alzheimer's disease, etc.) to boost an immune response in a subject. Some embodiments are of use as a therapeutic or as a prophylactic against a medical condition in a subject. In other embodiments, constructs may be generated for use in vaccination against viral diseases. In further embodiments, constructs may be generated for use in vaccines to protect from a pathogen. Some embodiments described herein concern constructs to protect against and/or treat a subject exposed to or having an influenza infection.

Influenza Virus

Influenza is an orthomyxovirus. Three genera, types A, B, and C of influenza currently exist. Types A and B are the most clinically significant, causing mild to severe respiratory illness. Type A viruses exist in both human and animal populations, with significant avian and swine reservoirs. Although relatively uncommon, it is possible for nonhuman influenza A strains to infect humans by jumping from their natural host. In one specific example, the highly lethal Hong Kong avian influenza outbreak in humans in 1997 was due to an influenza A H5N1 virus that was an epidemic in the local poultry population at that time. In this case, the virus killed six of the 18 patients shown to have been infected.

Annual seasonal influenza A or B virus infections have a significant impact on humanity both in terms of death, between 500,000 and 1,000,000 worldwide each year and economic impact resulting from direct and indirect loss of productivity during infection.

In 2009, an influenza pandemic erupted. The virus isolated from patients in the United States was found to be made up of genetic elements from four different flu viruses—North American Mexican influenza, North American avian influenza, human influenza, and swine influenza virus typically found in Asia and Europe. This new strain appears to be a result of reassortment of human influenza and swine influenza viruses, in all four different strains of subtype H1N1.

In certain embodiments, a virus can include an influenza virus infection, for example, influenza type A, B or C or subtype or strain thereof. Some embodiments include, but are not limited to, influenza A, H1N1 subtype or H1N1 of swine origin and strains. Other influenza A viruses may include, but are not limited to, H2N2, which caused Asian Flu in 1957; H3N2, which caused Hong Kong Flu in 1968; H5N1, a current pandemic threat; H7N7, which has unusual zoonotic potential; H1N2, endemic in humans and pigs; H9N2; H7N2; H7N3, H10N7 or combinations thereof.

Influenza A and B each contain 8 segments of negative sense ssRNA. Type A viruses can also be divided into antigenic subtypes on the basis of two viral surface glycoproteins, hemagglutinin (HA) and neuraminidase (N). There are currently 15 identified HA subtypes (designated H1 through H15) and 9 NA subtypes (N1 through N9) all of which can be found in wild aquatic birds. Embodiments of the present invention can include constructs having one or more of any influenza gene segment subtype known in the art. Of all the possible (e.g. over 135) combinations of HA and NA, four (H1N1, H1N2, H2N2, and H3N2) have widely circulated in the human population since the virus was first isolated in 1933. Two of the more common subtypes of influenza A currently circulating in the human population are H3N2 and H1N1.

New type influenza A strains emerge due in part to genetic drift that can result in slight changes in the antigenic sites on the surface of the virus. This shift can lead to the human population experiencing epidemics of influenza infection every year. More drastic genetic changes can result in an antigenic shift (a change in the subtype of HA and/or NA) resulting in a new subtype capable of rapidly spreading in a susceptible population.

Subtypes are sufficiently different as to make them non-crossreactive with respect to antigenic behavior; prior infection with one subtype (e.g. H1N1) can lead to no immunity to another (e.g. H3N2). It is this lack of crossreactivity that in certain cases allows a novel subtype to become pandemic as it spreads through an immunologically naïve population.

Although relatively uncommon, it is possible for nonhuman influenza A strains to transfer from their "natural" reservoir to humans. In one example, the highly lethal Hong Kong avian influenza outbreak in humans in 1997 was due to an influenza A H5N1 virus that was an epidemic in the local poultry population at that time. This virus transferred to other hosts (e.g. humans) from contaminated chickens.

Some embodiments of the present invention report vaccine compositions including, but not limited a poxvirus and one or more poxvirus secretory signals associated with one or more non-poxvirus peptides. In certain embodiments, a vaccine composition may include a modified or attenuated poxvirus associated with one or more secretory poxvirus secretory signals associated with one or more non-poxvirus peptides. In other embodiments, recombinant modified vaccinia Ankara (MVA) vector associated with one or more poxvirus secretory signals associated with one or more non-poxvirus peptides. In other embodiments, a vaccine composition may include a recombinant modified vaccinia Ankara (MVA) vector associated with one or more influenza-associated peptides where at least one of the one or more influenza-associated peptides is associated with a poxvirus secretory signal. For example, a vaccine composition can include recombinant modified vaccinia Ankara (MVA) vector expressing influenza virus components. In accordance with this vaccine composition, an MVA construct expressing one or more influenza-associated antigens may be generated (e.g. HA, NP, NA, M, P, etc.) for use to vaccinate a subject against influenza. It is contemplated that vaccine constructs can contain a more conserved or highly conserved influenza genetic region or influenza associated peptide alone or in combination with a more variable influenza associated peptide. Alternatively, a vaccine construct contemplated herein can contain a peptide or the entire segment of an internal influenza gene region (e.g. M) or an externally (e.g. HA) exposed gene region.

In certain embodiments, influenza virus is selected from the group consisting of influenza A H3N2, influenza A H1N1, influenza A H1N1 swine-origin, avian influenza A H5N1, and influenza B.

Certain embodiments of the present invention report compositions having constructs directed against poxviruses. For example, vaccine compositions may be directed to the prevention or reduced incidence of conditions associated with poxvirus or influenza viruses.

Poxviridae

Poxviruses (members of the family Poxviridae) are viruses that can, as a family, infect both vertebrate and invertebrate animals. There are four known genera of poxviruses that may infect humans: orthopox, parapox, yatapox, molluscipox. Orthopox include, but are not limited to, variola virus, vaccinia virus, cowpox virus, monkeypox virus, and smallpox. Parapox include, but are not limited to, orf virus, pseudocowpox, bovine papular stomatitis virus; Yatapox: tanapox virus, yaba monkey tumor virus. Molluscipox include, but are not limited to, molluscum contagiosum virus (MCV). Some of the more common oixviruses are vaccinia and molluscum contagiousum, but monkeypox infections seem to be on the rise.

Poxvirus family, vaccinia virus, has been used to successfully vaccinate against smallpox virus. Vaccinia virus is also used as an effective tool for foreign protein expression to elicit strong host immune response. Vaccinia virus enters cells mainly by cell fusion, although currently the receptor is not known. Virus contains three classes of genes, early, intermediate and late that are transcribed by viral RNA polymerase and associated transcription factors. Diseases caused by pox viruses have been known about for centuries.

Orthopoxviruses

Certain embodiments of the present invention may include using modified or attenuated orthopoxviruses or orthopoxvirus associated genetic elements or peptides in vaccine compositions. Orthopoxvirus is a genus of the Poxviridae family, that includes many agents isolated from mammals, including, but not limited to, vaccinia, monkeypox, cowpox, camelpox, seal poxvirus, buffalo poxvirus, raccoon poxvirus, skunk poxvirus, vole poxvirus and ectromelia viruses. Members of Poxviridae have large linear double-stranded DNA, with genome sizes ranging from 130 to 300 kbp. One of the members of the genus is variola virus, which causes smallpox. Smallpox was previously eradicated using another orthopoxvirus, the vaccinia virus, as a vaccine.

Modified Vaccinia Virus Ankara (MVA)

Some embodiments in the present invention report compositions and methods of use of recombinant vaccinia viruses derived from attenuated poxviruses that are capable of expressing predetermined or preconstucted genes or gene segments. Those skilled in the art recognize that other attenuated poxviruses can be generated by serial passage in cell culture or by deliberate deletion of poxviral genes. In certain embodiments, predetermined genes may be inserted at the site of a naturally occurring deletion in the MVA genome. In other embodiments, recombinant MVA viruses can be used, for example, for the production of polypeptides (e.g. antigens) or for encoding antigens of use for vaccine compositions capable of inducing an immune response in a subject administered the vaccine compositions.

In certain embodiments, modified or attenuated poxviruses (e.g. modified vaccinia Ankara (MVA), NYVAC, LC16m8, or CV1-78), can be used in a subject (e.g. mammals such as humans) as a delivery system for pre-boost, boost or post-boost vaccination in order to induce immunity to a pathogen in the subject. Previously, MVA was administered to over 120,000 individuals and proven to be a safe and effective vaccine against smallpox. In certain embodiments, recombinant MVA vaccine candidates have been shown to induce protective humoral and cellular immunity against diseases caused by viruses, bacteria, parasites, or tumors from which antigens or peptides were derived. Additional features that make MVA a suitable vector include its ability to induce protective immune responses when administered by different routes and its genetic and physical stability properties.

Translational Control Sequences

Some embodiments may include an optional enhancer, for example, a translation control sequence. In certain embodiments, a translation control sequence may include an internal ribosomal entry site (IRES) (e.g. EMCV-IRES). Viral IRESs are classified into four groups: Group 1 (Cricket paralysis virus (CrPV), *Plautia* stall intestine virus (PSIV) and Taura syndrome virus (TSV)); Group 2 (Hepatitis C virus, (HCV), classical swine fever virus (CSFV) and porcine teschovirus 1 (PTV-1)); Group 3 (encephalomyocarditis virus (EMCV), foot-and-mouth-disease virus (FMDV) and Theiler's Murine Encephalomyelitis virus (TMEV)); and Group 4 (poliovirus (PV) and rhinovirus (RV)). In other embodiments, viral untranslated regions (UTRs) found 5' to viral coding sequences can be used to direct translation. Any translation control sequence of use in viral constructs known in the art is contemplated.

Secretory Signals

Alternatively, embodiments of the present invention may include constructs having one or more poxvirus secretory signal sequences in combination with other elements. Translation control sequences and/or poxvirus secretory signals were demonstrated to increase efficacy of certain vaccine constructs. In some embodiments, one or more poxvirus secretory signal sequences of constructs disclosed herein can include, but are not limited to, secretory signal sequence in the poxvirus genes C13L (putative), B8R (soluble interferon gamma receptor), B19R (interferon a/b receptor), A39R (semaphoring), M2L (putative), C13L (putative), C19L or other secretory signal sequences known in the art. Constructs disclosed herein can contain one or more secretory signal sequence.

In some embodiments, when designing a construct, such that a protein is expressed, it may be necessary to incorporate into a first nucleic acid region a DNA sequence encoding a signal sequence, for example, in cleavable form, where the expressed protein is desired to be secreted. Without limiting embodiments of the present invention to any one theory or mode of action, a signal sequence can be a peptide that is present on proteins destined either to be secreted or to be membrane bound. These signal sequences can be found at the N-terminus of the protein and are generally cleaved from a mature form of a protein. The signal sequence generally interacts with the signal recognition particle and directs the ribosome to the endoplasmic reticulum where co-translational insertion takes place. Where the signal sequence is cleavable, it is generally removed by for example, a signal peptidase.

The choice of signal sequence which is to be utilized may depend on the requirements of the particular situation and can be determined by the person of skill in the art. In the context of the exemplification provided herein, but without being limited in that regard, tPA, a poxvirus signal sequences from C13L or B8R may be used to facilitate secretion of a peptide, protein or construct of interest. If a membrane protein is desired, both a 5' cleavable signal sequence at the amino end of the protein and a non-cleavable membrane anchor at the 3'(carboxy) end of the protein may be needed. These could be provided within the vector or one or both could be encoded by the DNA of the protein of interest.

Some embodiments of the present invention include, but are not limited to, compositions including one or more constructs. A construct may be designed to produce proteins that are cytoplasmically retained, secreted or membrane bound. Deciding what form a protein of interest may need to take can depend on the functional requirement of the protein. For example, anchored cell surface expression of a protein of interest can provide a convenient way for screening for molecules that interact with a protein or peptide of interest such as antibodies, antagonists, agonists or the like particularly to the extent that the protein is expressed on the membrane of an adherent cell type. Still further membrane anchored forms of proteins may be suitable for administration to a subject for example, for generating monoclonal antibodies to the protein. This may be due to host cells providing a convenient source of the protein that is likely to be correctly folded and have appropriate post-translational modifications, for example, glycosylation and disulphide bond formation. In addition, a host cell may provide adjuvant properties, for example, antigenic differences from a recipient subject, notably in major histocompatibility complexes (MHC).

Alternatively, secreted proteins can be suitable where a protein is to be harvested and purified. A nucleic acid molecule encoding a signal sequence may be positioned in the construct at any suitable location which can be determined as a matter of routine procedure by a person of skill in the art. In some embodiments, a signal sequence may be positioned immediately 5' to the nucleic acid sequence encoding a peptide, protein or construct of interest (such that it can be expressed as an immediately adjacent fusion with the protein of interest) but 3' to a promoter such that expression of a signal sequence is placed under control of the promoter. A nucleic acid sequence encoding a signal sequence can form part of a first nucleic acid region of a construct.

It is contemplated herein that constructs and vaccine compositions disclosed can be used as therapies for conditions such as diabetes, Alzheimer's and cancer or other condition. Constructs may be generated for use in vaccines that protect against or as therapies for certain conditions (e.g. for cancer, diabetes, Alzheimer's disease, etc.). In addition, vaccine compositions and pre-boost compositions described herein can be used in subjects to boost their immune system.

Tumor Markers

Tumor markers and associated tumor peptides are contemplated for using in constructs described herein. Tumor markers and peptides associated with tumors (e.g. non-poxvirus peptides) can be used in combination with elements described herein in order to develop vaccines to treat or prevent cancer in a subject. Some tumor markers include, but are not limited to the following, 707-AP=707 alanine proline AFP=alpha (α)-fetoprotein, ART−4=adenocarcinoma antigen recognized by T cells 4, BAGE=B antigen; b-catenin/m, β-catenin/mutated, Bcr-abl=breakpoint cluster region-Abelson, CAMEL=CTL-recognized antigen on melanoma, CAP-1=carcinoembryonic antigen peptide-1, CASP-8=caspase-8, CDC27m=cell-divisioncycle, 27 mutated, CDK4/m=cycline-dependent kinase 4 mutated, CEA=carcinoembryonic antigen, CT=cancer/testis (antigen), Cyp-B=cyclophilin B, DAM=differentiation antigen melanoma (the epitopes of DAM-6 and DAM-10 are equivalent, but the gene sequences are different. DAM-6 and DAM-10, ELF2M=elongation factor 2 mutated, ETV6–AML1=Ets, variant gene 6/acute myeloid leukemia 1 gene ETS, G250=glycoprotein 250 GAGE=G antigen, GnT-V=N-acetylglucosaminyltransferase V, Gp100=glycoprotein 100 kD, HAGE=helicose antigen, HER-2/neu=human epidermal receptor-2/neurological, HLA-A*0201–R1701=arginine (R) to isoleucine (I) exchange at residue 170 of the α-helix of the α2-domain in the HLA-A2 gene, HPV-E7=human papilloma virus E7, HSP70-2M=heat shock protein 70-2 mutated, HST-2=human signet ring tumor–2, hTERT or hTRT=human telomerase reverse transcriptase, iCE=intestinal carboxyl, sterase, KIAA0205=name of the gene as it appears in databases, LAGE=L antigen, LDLR/FUT=low density lipid receptor/GDP-L-fucose: β-D-galactosidase 2-α-Lfucosyl-transferase, MAGE=melanoma antigen, MART-1/Melan-A=melanoma, antigen recognized by T cells-1/Melanoma antigen A, MC1R=melanocortin 1 receptor, Myosin/m=myosin mutated, MUCi=mucin, MUM-1, -2, -3=melanoma, ubiquitous mutated 1, 2, 3 NA88-A=NA cDNA clone of patient M88, NY-ESO-1=New York—esophageous 1, P15=protein 15, p190 minor bcr-abl=protein of 190, KD bcr-abl, Pml/RARa=promyelocytic leukaemia/retinoic acid receptor α, FRAME=preferentially expressed antigen of melanoma, PSA=prostate-specific antigen, PSM=prostate-specific membrane antigen, RAGE=renal antigen, RU1 or RU2=renal, ubiquitous 1 or 2, SAGE=sarcoma antigen, SART-1 or SART-3=squamous antigen, rejecting tumor 1 or 3, TEL/AML1=translocation Ets-family leukemia/acute myeloid, leukemia 1, TPI/m=triosephosphate isomerase mutated, TRP-1=tyrosinase related, protein 1, or gp75, TRP-2=tyrosinase related protein 2, TRP-2/INT2=TRP-2/intron, WTI=Wilms' tumor gene and any other tumor antigen known in the art. In certain embodiments, a pre-boost having an MVA construct can be used alone or prior to administering a vaccine having a tumor antigen derived peptide to a subject in need thereof.

Anti-microbial peptides are contemplated of use in constructs disclosed herein. Anti-microbial peptides can be expressed in constructs described and used alone or after a subject is administered a pre-immune boost to treat or prevent an infection.

Selection Markers

In certain embodiments, additional selection markers may be used, for example, one may insert any number of selection markers which may be designed, for example, to facilitate the use of the vectors in a variety of ways, such as purification of a molecule of interest. For example, glutathione S-transferase (GST) gene fusion system provides a convenient means of harvesting a construct, protein or peptide of interest. Without limiting to any one theory or mode of action, a GST-fusion protein can be purified, by virtue of the GST tag, using glutathione agarose beads. Embodiments of the present invention should be understood to extend to constructs encoding a secretable GST-molecuie fusion. This could be achieved, for example, by designing the sequence of a first nucleic acid region such that it encodes a cleavable signal sequence fused to a cleavable GST which is, in turn, fused to the molecule of interest. In another example, a fusion tag could be used. In accordance with these embodiments, a fusion tag can be between 360 bp of protein A (allowing purification of the secreted product) and beta lactamase (a bacterial enzyme which allows testing of supernatants by a simple colour reaction). Beta lactamase facilitates selection of an assay for a molecule of interest in the absence of an assay for molecule of interest. The protein A/beta lactamase fusion can be separated from the molecule of interest by a cleavage site to facilitate cleavage, so that after the molecule is purified, the tag can be easily removed.

Other fusion tags that could be included to facilitate purification of a molecule or construct of interest of use for embodiments disclosed herein can include, but are not limited to, staphylococcal protein A, streptococcal protein G, hexa-histidine, calmodulin-binding peptides and maltose-binding protein (e.g. the latter is also useful to help ensure correct folding of a molecule of interest). Yet another selectable marker may include an antibiotic resistance gene. Other embodiments may include an antibiotic resistance gene. These genes have previously been utilized in the context of bicistronic vectors as the selection marker or HAT-based selectable bicistronic vector may be used.

Electrophoresis

Electrophoresis may be used to separate molecules (e.g. large molecules such as proteins or nucleic acids) based on their size and electrical charge. There are many variations of electrophoresis known in the art. A solution through which the molecules move may be free, usually in capillary tubes, or it may be embedded in a matrix. Common matrices include polyacrylamide gels, agarose gels, and filter paper.

Proteins, peptides and/or antibodies or antibody fragments thereof may be detected partially or wholly purified, or analyzed by any means known in the art. In certain embodiments, methods for separating and analyzing molecules may be used such as gel electrophoresis and elution or column chromatography or other separation/purification methods.

Any method known in the art for detecting, analyzing and/or measuring levels of antibodies or antibody fragments may be used in embodiments reported herein. For example, assays for antibodies or antibody fragments may include, but are not limited to, ELISA assays, chemiluminescence assays, flow cytometry, electroelution and other techniques known in the art.

Imaging Agents and Radioisotopes

In certain embodiments, the claimed proteins or peptides may be linked to a secondary binding ligand or to an enzyme (an enzyme tag) that will generate a fluorescent, a luminescent, or a colored product upon contact with a substrate. Examples of suitable enzymes include luciferase, green fluorescent protein, urease, alkaline phosphatase, (horseradish) hydrogen peroxidase and glucose oxidase. The use and identification of such labels is well known to those of skill in the art.

In other embodiments, labels or molecules capable of detecting peptides, antigens, constructs, antibodies or antibody fragments may include using aptamers. Methods for making and using aptamers are well known in the art and these methods and uses are contemplated herein. In addition, aptamers may be generated against construct elements disclosed herein and used for any purpose (e.g. purification, detection, modifying effects of the construct etc).

Some embodiments can include methods for detecting and/or making polyclonal or monoclonal antibodies produced by a subject exposed to vaccine compositions disclosed in some embodiments of the present invention. For example, antibodies produced capable of inducing passive immunity to a subject may be isolated, analyzed and/or produced as a whole antibody or fragment thereof, or a polyclonal or a monoclonal antibody. Any means for producing or analyzing these antibodies or antibody fragments known in the art are contemplated.

Nucleic Acid Amplification

Nucleic acid sequences used as a template for amplification can be isolated from viruses, bacteria, cells or cellular components contained in the biological sample, according to standard methodologies. A nucleic acid sequence may be genomic DNA or fractionated or whole cell RNA. Where RNA is used, it may be desired to convert the RNA to a complementary cDNA. In one embodiment, the RNA is whole cell RNA and is used directly as the template for amplification. Any method known in the art for amplifying nucleic acid molecules are contemplated (e.g. PCR, LCR, Qbeta Replicase etc).

Expressed Proteins or Peptides

Genes can be expressed in any number of different recombinant DNA expression systems to generate large amounts of the polypeptide product, which can then be purified and used in methods and compositions reported herein. Any method known in the art for generating and using constructs is contemplated. In certain embodiments, genes or gene fragments encoding one or more polypeptide may be inserted into an expression vector by standard cloning or subcloning techniques known in the art.

Some embodiments, using a gene or gene fragment encoding a polypeptide may be inserted into an expression vector by standard subcloning techniques. An expression vector may be used which produces the recombinant polypeptide as a fusion protein, allowing rapid affinity purification of a peptide or protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.).

Pharmaceutical Compositions and Routes of Administration

Aqueous compositions of some embodiments herein can include an effective amount of a therapeutic protein, peptide, construct, epitopic core region, stimulator, inhibitor, and the like, dissolved or dispersed in a pharmaceutically acceptable carrier or aqueous medium. Aqueous compositions of vectors expressing any of the foregoing are also contemplated. The phrases "pharmaceutically or pharmacologically acceptable" refer to molecular entities and compositions that do not produce an adverse, allergic or other untoward reaction when administered to an animal, or a human, as appropriate.

Aqueous compositions of some embodiments herein can include an effective amount of a therapeutic protein, peptide, construct, an effective amount of the compound, dissolved or dispersed in a pharmaceutically acceptable carrier or aqueous medium. Such compositions can also be referred to as inocula. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds or constructs will then generally be formulated for parenteral administration, e.g., formulated for injection via the intravenous, intramuscular, sub-cutaneous, intralesional, intranasal or even intraperitoneal routes. Any route used for vaccination or boost of a subject can be used. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Pharmaceutical forms suitable for injectable use can include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

If formulations or constructs disclosed herein are used as a therapeutic to boost an immune response in a subject, a therapeutic agent can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions can be prepared by incorporating the active compounds or constructs in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions can be administered in a manner compatible with the dosage formulation and in such amount as is therapeutically effective. The formulations are easily administered in a variety of dosage forms, such as the type of injectable solutions described above, but slow release capsules or microparticles and microspheres and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580).

The term "unit dose" refers to physically discrete units suitable for use in a subject, each unit containing a predetermined quantity of the construct composition or boost compositions calculated to produce desired responses, discussed above, in association with its administration, e.g., the appropriate route and treatment regimen. The quantity to be administered, both according to number of treatments or vaccinations and unit dose, depends on the subject to be treated, the state of the subject and the protection desired. The person responsible for administration will, in any event, determine the appropriate dose for the individual subject. For example, a subject may be administered a construct composition disclosed herein on a daily or weekly basis for a time period or on a monthly, bi-yearly or yearly basis depending on need or exposure to a pathogenic organism or to a condition in the subject (e.g. cancer).

The active therapeutic agents may be formulated within a mixture to comprise about 0.0001 to 1.0 milligrams, or about 0.001 to 0.1 milligrams, or about 0.1 to 1.0 or even about 10 milligrams per dose or so. Alternatively active agents (e.g. constructs) may be formulated to comprise a certain number of constructs per dose known to produce a desired effect in a subject. Multiple doses can also be administered.

In addition to the compounds formulated for parenteral administration, such as intravenous, intradermal or intramuscular injection, other pharmaceutically acceptable forms include, e.g., tablets or other solids for oral administration; liposomal formulations; time release capsules; biodegradable and any other form currently used.

One may also use intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and can include, for example, antibiotics and antihistamines and are used for asthma prophylaxis.

Additional formulations which are suitable for other modes of administration can include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

Kits

Further embodiments concerns kits for use with the methods and compositions described herein. Some embodiments concern kits having one or more vaccine or boost compositions of use to prevent or treat subjects having or exposed to a pathogen or have a condition. In certain embodiments, a pathogen can include a viral, bacterial, fungal, or protozoan derived pathogen. A condition can include a chronic condition or a condition like cancer. Other embodiments concern kits having vaccine compositions of use to prevent or treat subjects having or exposed to influenza or poxvirus. Kits can be portable, for example, able to be transported and used in remote areas. Other kits may be of use in a health facility to treat a subject having been exposed to a virus or suspected of being at risk of exposure to a pathogen (e.g. viral pathogen). Kits can include one or more construct compositions that can be administered before, during and/or after exposure to a pathogen. Other kits can include dehydrated formulations of constructs contemplated herein in order to prolong the halflife of the constructs (e.g. for stockpiling the vaccinations in the event of an outbreak or providing treatments to remote areas).

Other embodiments can concern kits for making and using molecular constructs described herein. In certain embodiments, compositions can include constructs having one or more of, attenuated or modified MVA and poxvirus secretory signals. Other constructs can also include at least one secretory signal sequence. Yet other embodiments can have a construct that includes translation control sequences (e.g. IRES). Other reagents for making and using constructs are contemplated.

Kits can also include a suitable container, for example, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the agent, composition and any other reagent containers in close confinement for commercial sale. Such containers may include injection or blow-molded plastic containers into which the desired vials are retained. Optionally, one or more additional agents such as other anti-viral agents, anti-fungal or anti-bacterial agents may be needed for compositions described, for example, for compositions of use as a vaccine.

Dose ranges used during vaccination can vary depending on the nature of the live attenuated vaccine and viral vector used. For recombinant poxviruses these doses can range between $10^5$-$10^7$ PFUs. In certain embodiments of the present invention, immunogenic doses can be as low as $10^2$ pfu. Frequency of vaccination can vary depending on the nature of the vaccine, the condition of the subject and also the route of administration used. One regimen can include a primary immunization (prime) followed up by a boost administration four to six weeks post-prime immunization. In certain embodiments of the present invention, improvements in antigen translation and expression can permit fewer and/or lower doses to be administered to a subject. Some embodiments concern intramuscular administration and/or intradermal vaccination of a subject.

Any method known to one skilled in the art may be used for large scale production of recombinant peptides or proteins. In accordance with these embodiments, large-scale production of MVA can be used. For example, master and working seed stocks may be prepared under GMP conditions in qualified primary CEFs. Cells may be plated on large surface area flasks, grown to near confluence and infected at selected MOI and vaccine virus purified. Cells may be harvested and intracellular virus released by mechanical disruption, cell debris removed by large-pore depth filtration and host cell DNA digested with endonuclease. Virus particles may be subsequently purified and concentrated by tangential-flow filtration, followed by diafiltration. The resulting concentrated bulk vaccine may be formulated by dilution with a buffer containing stabilizers, filled into vials, and lyophilized. For use, the lyophilized vaccine may be reconstituted by addition of diluent.

Poxviruses are known for their stability. The ability to lyophilize vaccinia for long term, room temperature storage and distribution was one of the key attributes that permitted widespread use of the vaccine and eradication of smallpox. Recently, it was demonstrated that Dryvax vaccinia virus stockpiled in the 60's was still potent after several decades. Procedures for lyophilization and storage of poxviruses are well know in the art and could be applied to the recombinant poxvirus vaccines for some embodiments disclosed herein.

The following examples are included to demonstrate certain embodiments presented herein. It should be appreciated by those of skill in the art that the techniques disclosed in the examples that follow represent techniques discovered to function well in the practices disclosed herein. However, those of skill in the art should, in light of the present disclosure, appreciate that many changes can be made in the certain embodiments which are disclosed and still obtain a like or similar result without departing from the spirit and scope herein.

EXAMPLES

Many constructs described herein were generated, separated and purified by methods disclosed herein (data not shown) for use in various studies. Some of these constructs are detailed in the descriptions below. In certain methods, constructs with and without influenza gene segments and peptides were generated and used in mouse models exposed to influenza challenges.

Example 1

In one exemplary method, a construct composition including an influenza segment and a vaccinia secretory segment was tested for induction of immune protection against influenza challenge. FIGS. 1A and 1B illustrate a mouse model vaccinated and challenged with a virus. Here, Balb/C mice were vaccinated with MVA/IRES/tPA/HA (107 pfu) and challenged with VN/1203 63 (A/Vietnam/1203/04 (H5N1)-$10^4$ TCID$_{50}$) days post-vaccination. A) Weight loss, and B) Lungs titers, day 4 post-challenge. An MVA construct expressing an influenza segment elicited protection against the viral challenge. All the MVA vectored plague vaccines tested in this study were shown to be completely safe in severe combined immuno-deficient (SCID) mice. MVA has been stockpiled for use as a second-generation smallpox vaccine, with superior safety to the original live, attenuated vaccinia strains. Thus, a recombinant MVA/IRES/tPA/influenza segment vaccine has the potential to simultaneously provide protection against smallpox and influenza.

Example 2

Figure 2A:
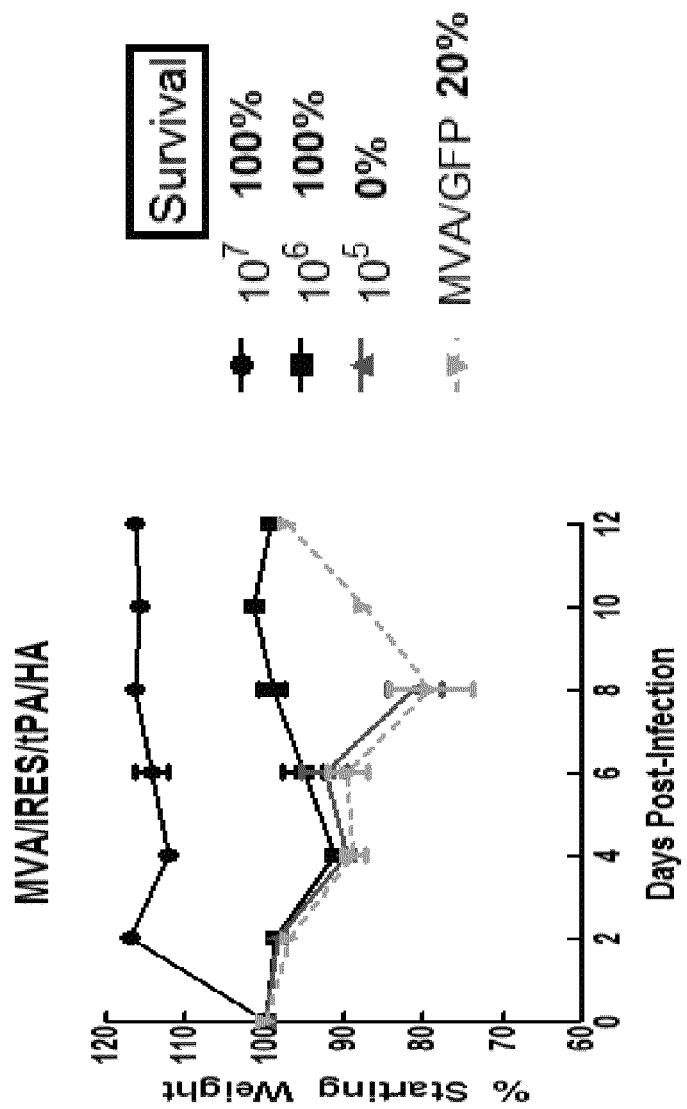
Figure 2B:
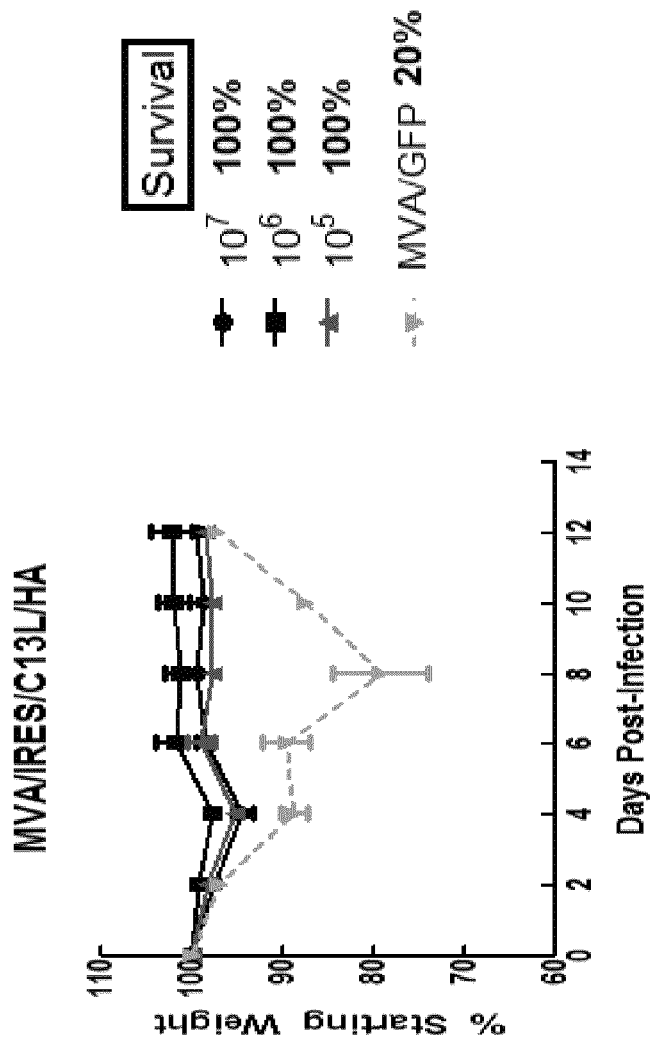
Figure 2C:
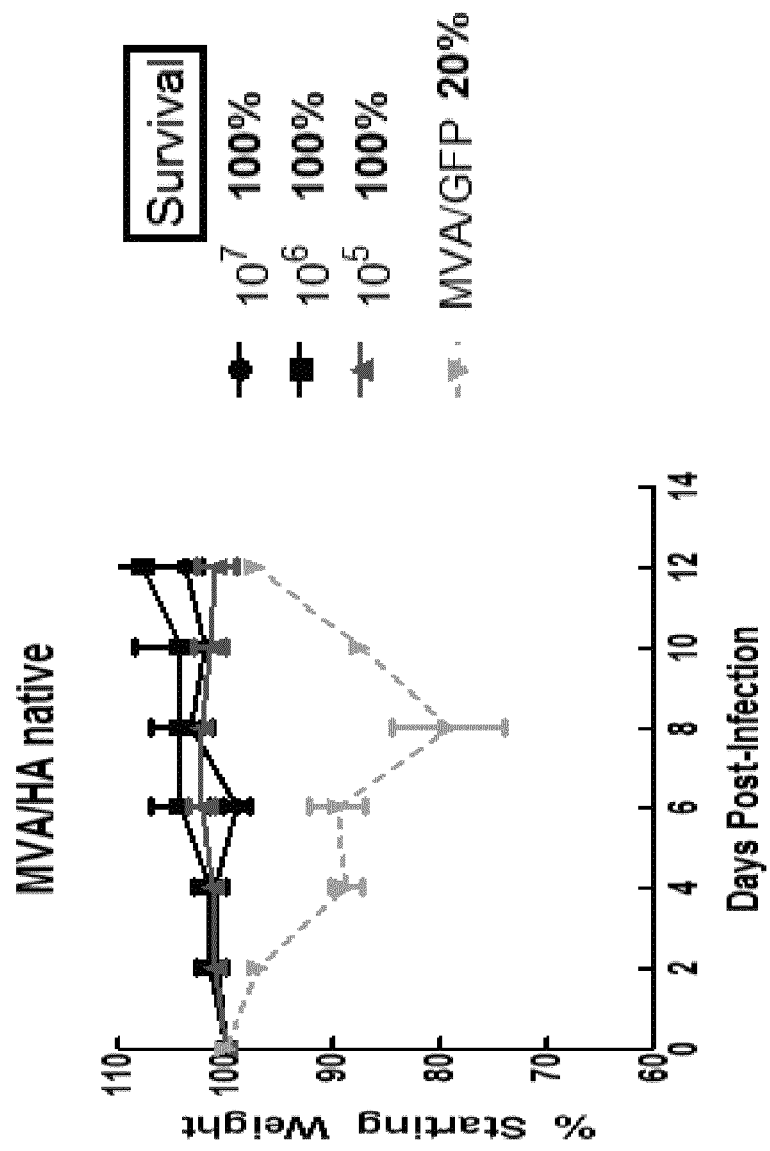

Dose Sparing: In another exemplary method, various constructs were tested in a range of doses to analyze their protective effects and to test some of the limitations in these dose ranges. FIGS. 2A-2C represents Balb/C mice (n=10) vaccinated ID with 105, 6 or 7 pfu and challenged with VN/1203 on day 63 post-vaccination. Weight loss curves are displayed for A) MVA/IRES/tPA/HA, B) MVA/IRES/C13L/HA, and C) MVA/HA native.

Example 3

Long-Term and Cross-Clade Protection

Figure 3:
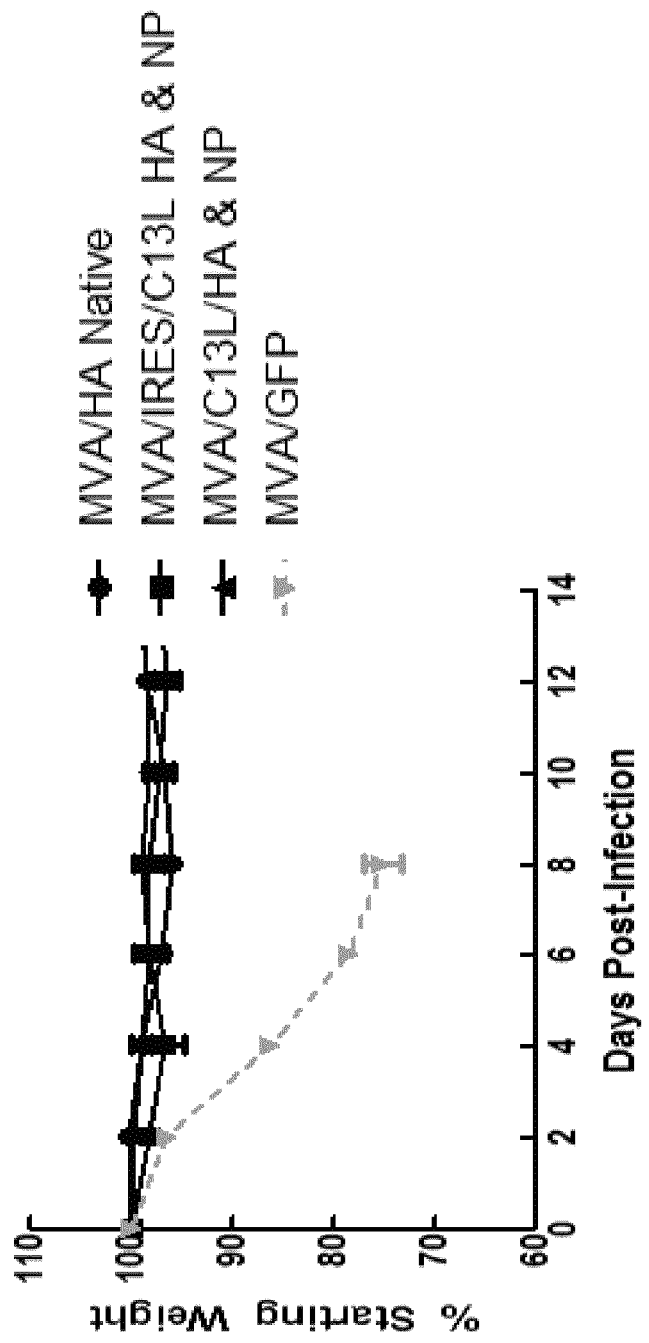
Figure 6A:
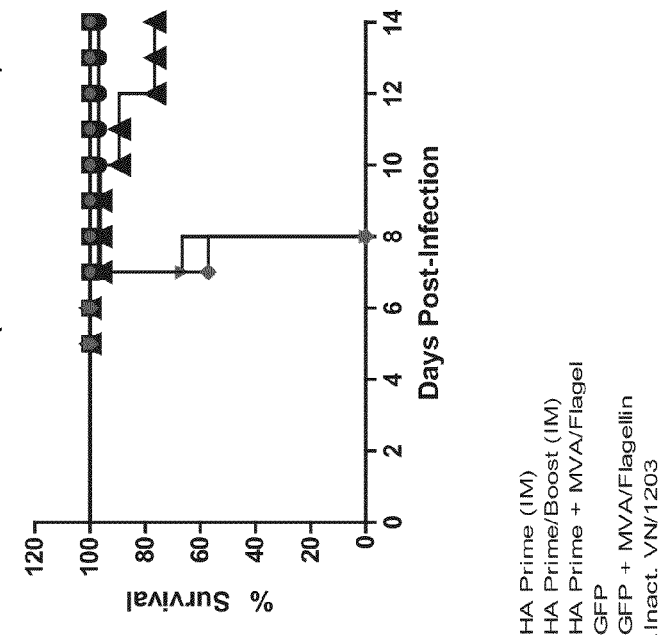
Figure 6B:
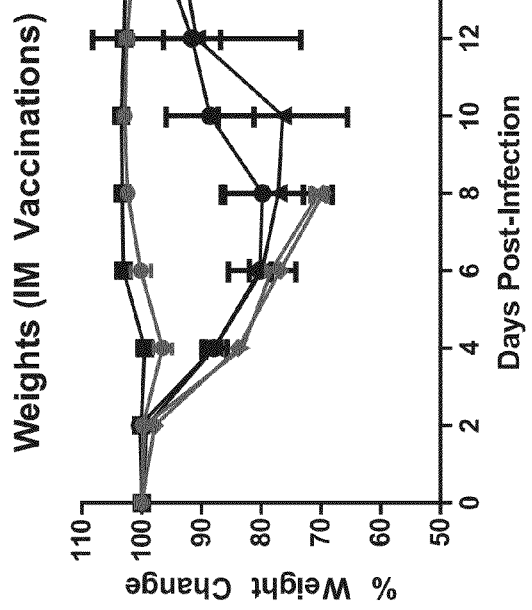
Figure 7A:
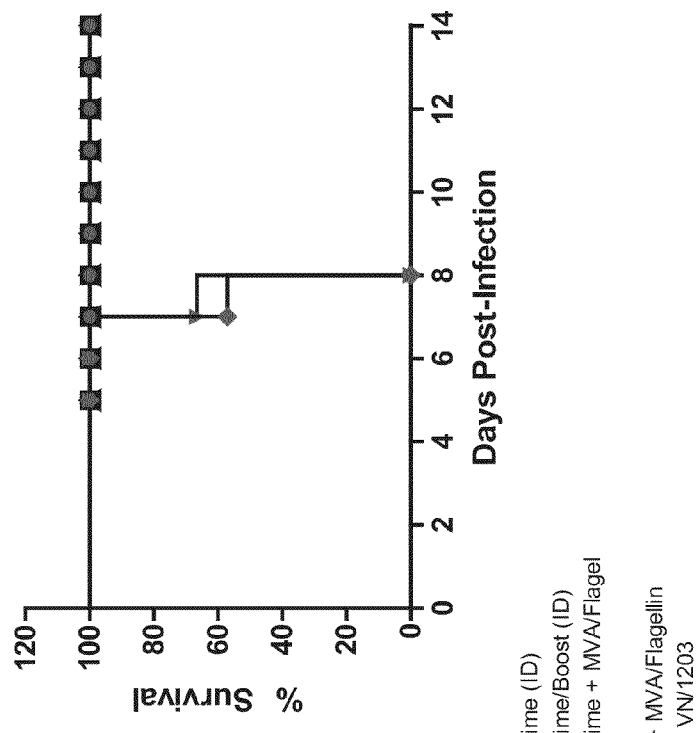
Figure 7B:
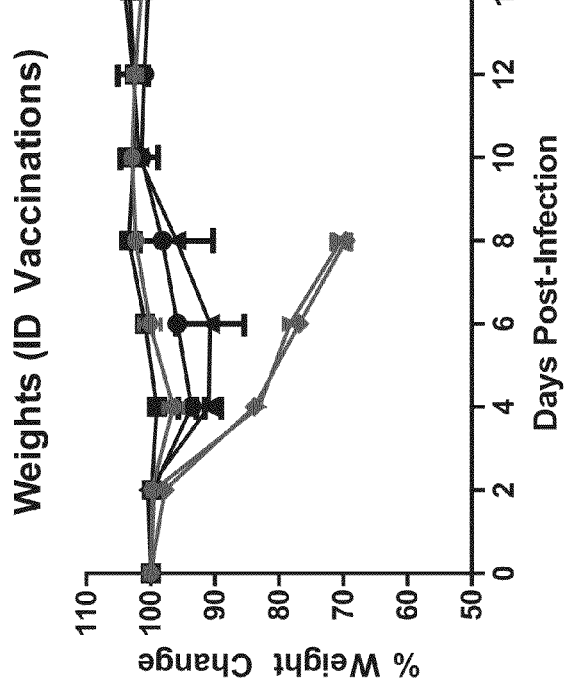
Figure 8B:
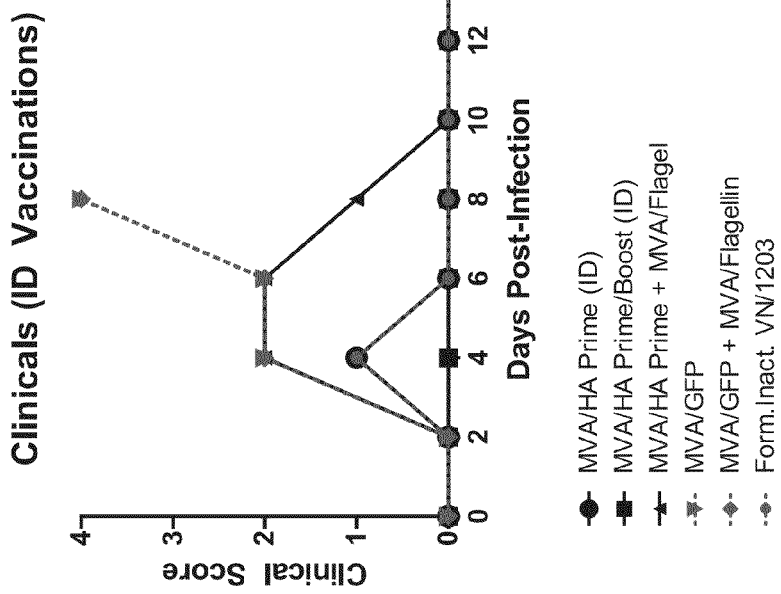
Figure 8A:
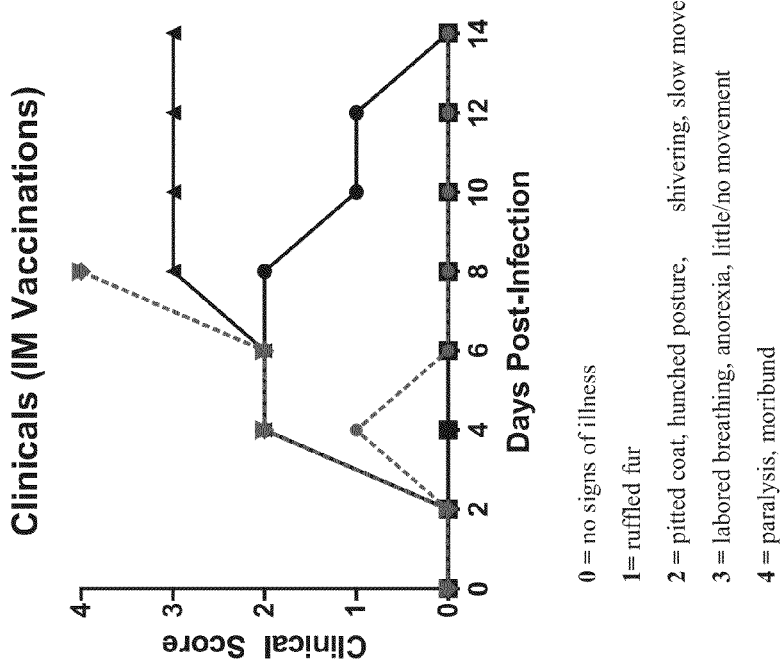
Figure 9:
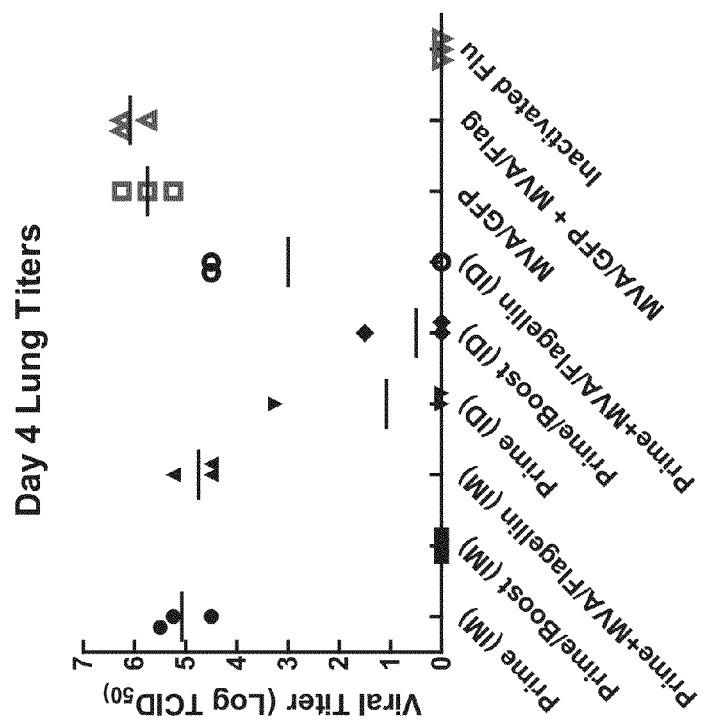
Figure 10A:
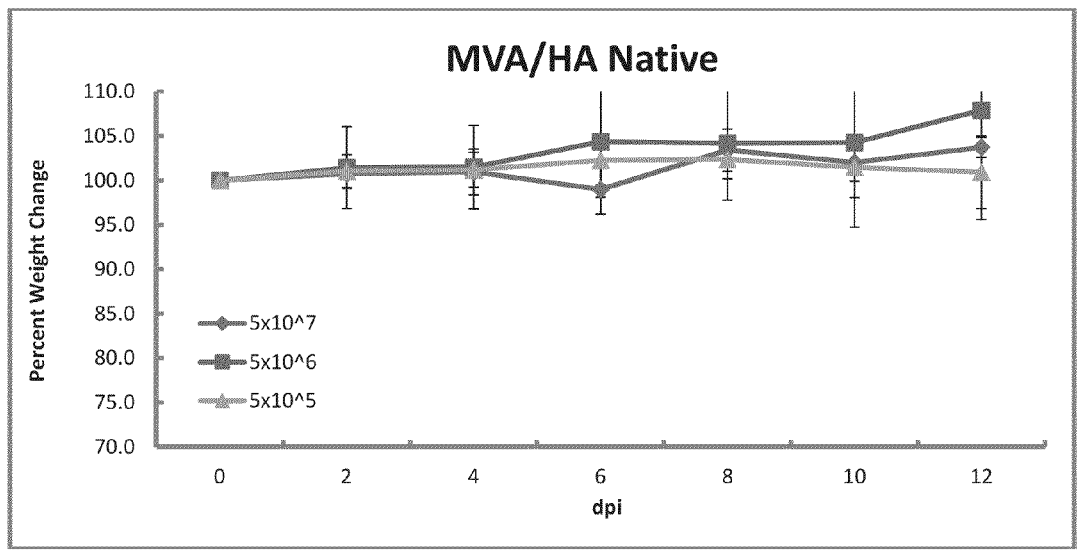
Figure 10B:
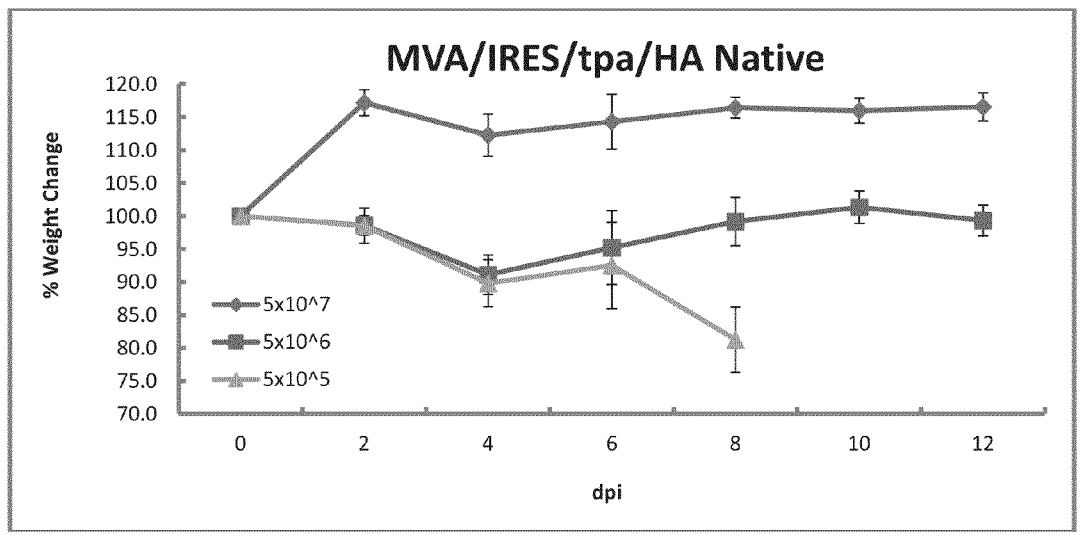
Figure 11A:
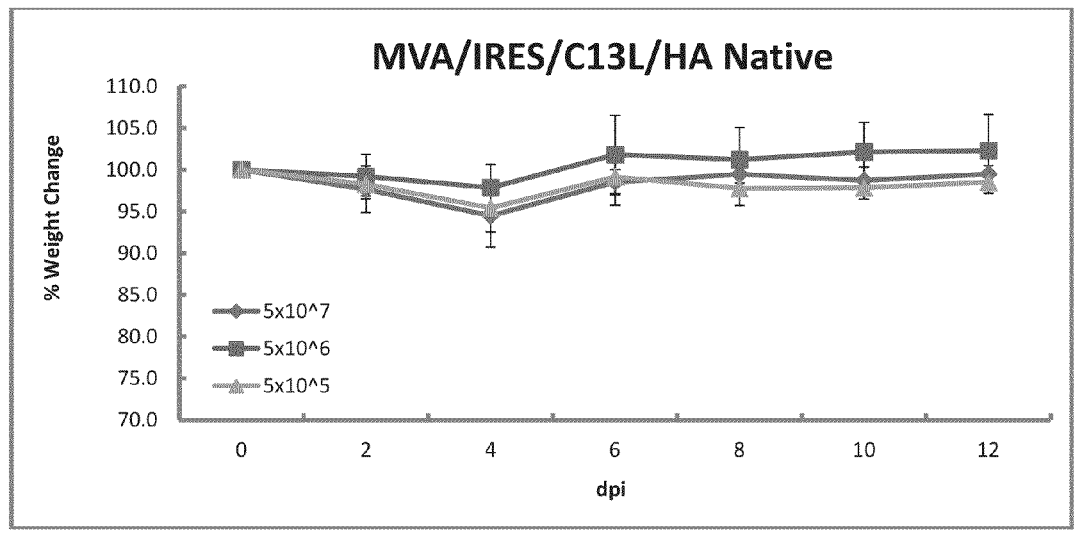
Figure 11B:
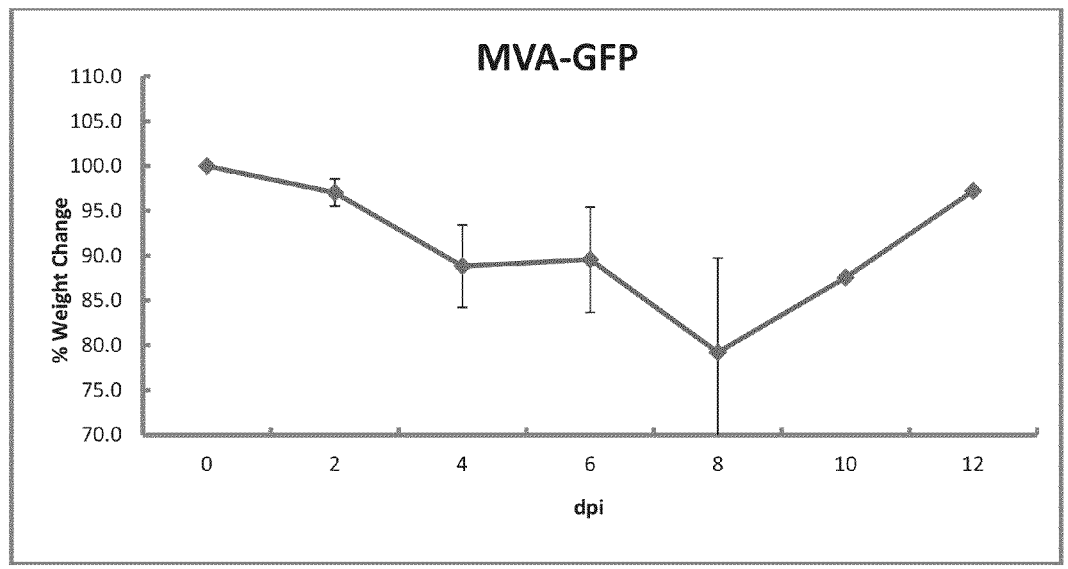
Figure 13A:
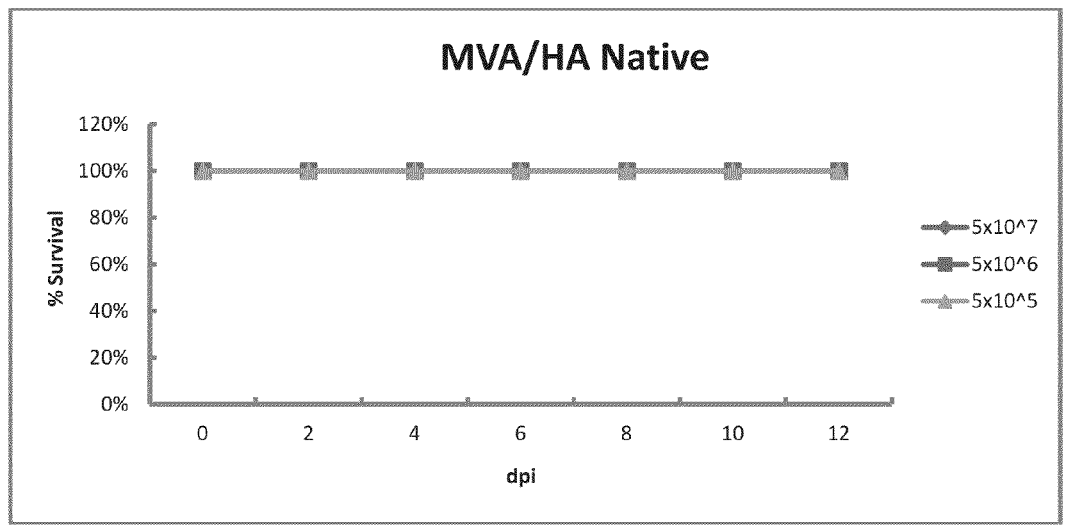
Figure 13B:
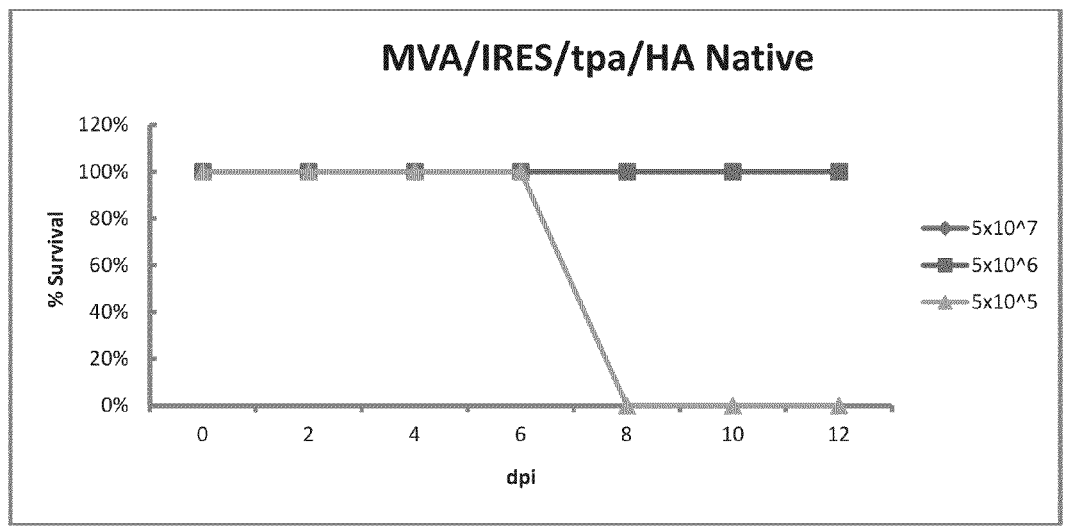

FIG. 3 illustrates that certain vaccine constructs presented herein provide long-Term Immunity. Balb/C mice (n=7) were intradermally (ID) vaccinated with 105 (HA) and/or 107 (NP) pfu and challenged with VN/1203 at 28 wks post-vaccination Example 4

Heterologous Clade 2 Challenge

Figure 4:
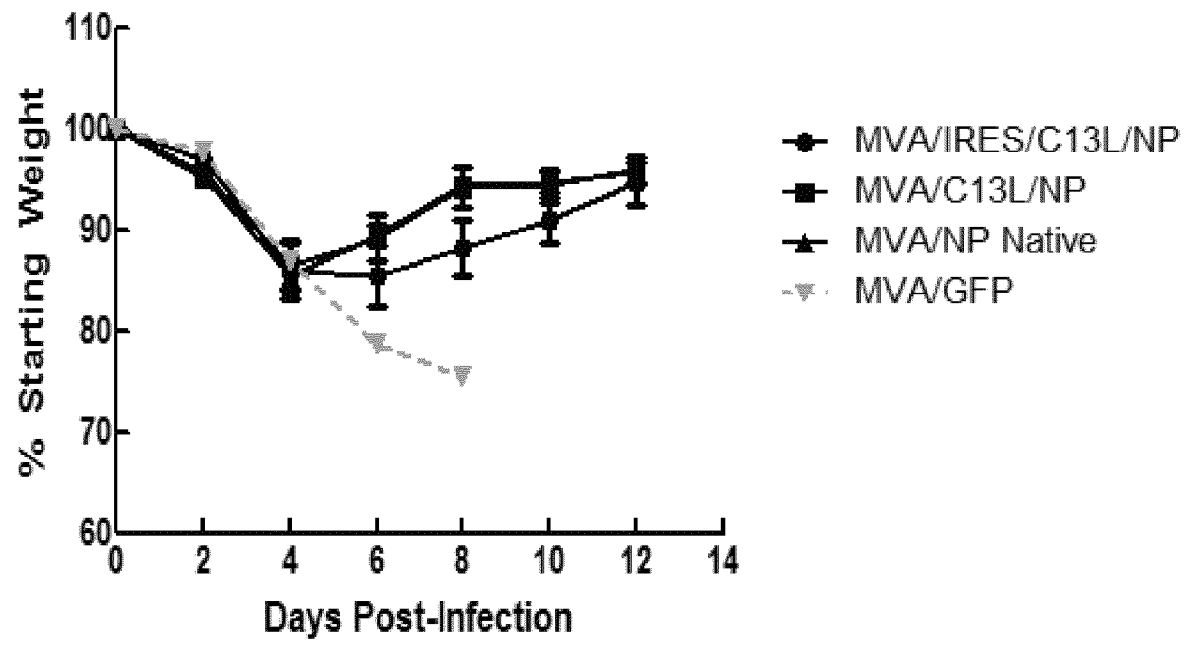

FIG. 4 illustrates cross-clade protection. Here, Balb/C mice (n=7) ID were vaccinated with $10^5$ (HA) or $10^7$ (NP) pfu/mouse, and challenged with VN/UT 28 wks post-vaccination.

Safety

Figure 5:
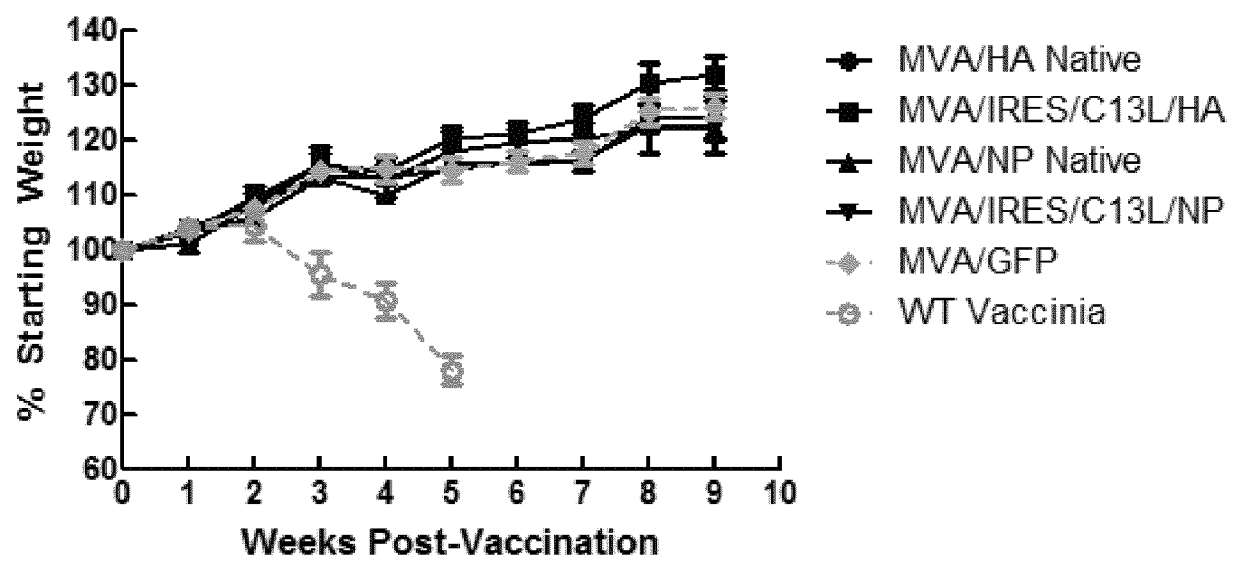

In another example, safeties of some of the vaccine constructs were assessed. FIG. 5 represents mice tested with certain constructs described herein. In this example, SCID/Balb/C mice (n=6) were IP inoculated with $10^8$ pfu/animal MVA-influenza constructs or $10^6$ pfu/animal Wild Type Vaccinia and monitored for morbidity and pox lesions for 6 weeks.

Experiments conducted in herein demonstrate that recombinant MVA influenza vaccines are safe & efficacious. It was demonstrated that single dose intradermal injection was able to provides 100% protection from lethal challenge. In addition, dose sparing introductions at about $5 \times 10^5$ offers 100% protection. In certain examples, protection was demonstrated to last up to 28 weeks. Other examples demonstrate that including NP in the constructs may provide cross-clade protection. Using a mouse model, it was demonstrated that recombinant MVA influenza vaccines are safe in SCID mice. These experiments demonstrate that MVA construct vaccinations may provide viable alternatives to traditional influenza vaccination, particularly for emerging virus subtypes.

B8R was used as a Vaccinia IFN-gamma soluble receptor. C13L is associated with a non-expressed protein in Vaccinia that may be a serpin homologue. As indicated these sequences are not present in MVA. The signal scores are equivalent or better than those for tPA. The scores are similar and not significantly different in the context of other antigens.

Putative Vaccinia signal sequences were analyzed and C13L signal was identified as a potent element for constructs generated and used herein. B8R signal could be more obvious as it is part of a known secreted Vaccinia protein.

Poxvirus Alternative Secretory Signals.

Alternative signal sequences from *orthopox* virus have been identified to replace tPA in certain constructs for example, for secretion enhancement from MVA. In this example, tPA cleavage site is correctly identified in F1 construct according to program signal P 3.0. Predicted cleavage after AG of NgoMIV site. Hidden Markov model (HMM) score of 98.8%.

Example 5

Exemplary Secretory Signal Sequences and Constructs

Some Options for constructs are outlined below.

C13L, exemplary secretory signal sequence

```
i.    VV-cop: 12510-12313
      (complete DNA sequence: 12510-11971).

ii.   Unknown protein function. Located
      near serpin homologues.

iii.  VV-cop version has a deletion following
      the signal peptide that
      causes a frame shift and unrelated
      protein sequence prior to
      termination 44 aa later. The DNA
      sequence is present in
      comparison to orthopox orthologs.
      The last 100 bp are present
      at 179670-179767 as an inverted repeat.
      Full coding sequence equivalent to VV-WR,
      loci 206.
```

```
iv.   Secretory signal:
            (SEQ ID NO: 1)
      1. 1 MMIYGLIACLIFVTSSIA^SP 20
      2. Signal peptide score = 10.3,
         probability = 6.1 x 10^-5, VV-WR 1.1 x 10^-3.
      3. Cleavage in F1 either AGA-DL (neural
         network) or SIA-SPAGAD (HMM) with 99.8%
         signal probability.
```

B8R exemplary secretory signal sequence

```
i.    VV-cop:

ii.   IFN-gamma soluble receptor gene:
      1. B8R is secreted from the cell
         to bind host IFN-gamma.
      2. Secretory signal:
              (SEQ ID NO: 2)
         a. 1 MRYIIILAVLFINSIHA^KI
         b. Signal peptide score = 10.5,
            probability = 4.1 x 10^-4
      3. Cleavage with F1 either KAG-ADL
         (neural network) or HA-KAGAD (HMM)
         with 99.1% signal probability.
```

Signal sequence design with and without IRES.

```
a. tPA without IRES.

b. With IRES, insert into XmaI site, not SalI site:
   i. C13L:
      1) For, 5' IRES, Xma, tm = 64.7:
                 (SEQ ID NO: 3)
         a) 5' TCGTCCCGGGTTATTTTCCACCATATTGCCGT 3'
      2) Rev, 3' C13L-Ngom, tm =
         64.7 with IRES sequence:
                 (SEQ ID NO: 4)
         a) 5' TCGTGCCGGCTGGACTAGCGATGGATGAAGTCACG
            AATATAAGACACGCTATTAATCCGTATATCATCATATTATC
            ATCGTGTTTTTCAAAGGA 3'
      3) pI41(pI4,C13L) created and
         annotated in CLC.
   ii. B8R:
      1) For, 5' IRES, Xma, tm = 64.7:
                 (SEQ ID NO: 5)
         a) 5' TCGTCCCGGGTTATTTTCCACCATATTGCCGT 3'
      2) Rev, 3' B8R-Ngom, tm =
         64.7 with IRES sequence:
                 (SEQ ID NO: 6)
         a) 5' TCGTGCCGGCTTTAGCGTGTATACTATTAATGAAC
            AAAACTGCGAGAATTATAATATATCTCATATTATCATCGTG
            TTTTTCAAAGGA 3'
      3) pI42(pI4,C13L) created and
         annotated in CLC.

c. Without IRES:
   i. C13L
      1) For: 5' C13L-Xma,Ngom,Nhe
                 (SEQ ID NO: 7)
         a) 5' CCGGGATGATGATATACGGATTAATAGCGTGTCTT
            ATATTCGTGACTTCATCCATCGCTAGTCCAGCCGGCG 3'
      2) Rev: 3' C13L-Xma,Ngom,Nhe
                 (SEQ ID NO: 8)
         a) 5' CTAGCGCCGGCTGGACTAGCGATGGATGAAGTCA
            CGAATATAAGACACGCTATTAATCCGTATATCATCATC 3'
      3) pI44(sel,C13L) created and
         annotated in CLC.
   ii. B8R
      1) For: 5' B8R-Xma,Ngom,Nhe
                 (SEQ ID NO: 9)
         a) 5' CCGGGATGAGATATATTATAATTCTCGCAGTTTTG
            TTCATTAATAGTATACACGCTAAAGCCGGCG 3'
      2) Rev: 3' B8R-Xma,Ngom,Nhe
                 (SEQ ID NO: 10)
         a) 5' CTAGCGCCGGCTTTAGCGTGTATACTATTAATGA
            ACAAAACTGCGAGAATTATAATATATCTCATC 3'
      3) pI45(sel,B8R) created and
         annotated in CLC.
```

Materials and Methods
Construction of MVA Recombinant Vaccines

The transfer plasmid was used to generate recombinant MVA expressing influenza gene segments. Any method known in the art can be used to generate these constructs.

Some Construct Test Groups include the following in the presence or absence of various native and non-IRES constructs (e.g. IRES, tPA, C13L and B8R).

1. MVA/HA (IM) prime
2. MVA/HA (IM) prime/boost
3. MVA/HA (IM) prime+MVA/flagellin (Adjuvant)
4. MVA/HA (ID) prime
5. MVA/HA (ID) prime/boost
6. MVA/HA (ID) prime+MVA/flagellin (Adjuvant)
7. MVA/GFP prime/boost (IM)
8. MVA/GFP prime/boost (IM) flagellin
9. Formalin Inactivated VN/1203 5 ng (IM) prime/boost Some of these constructs have been generated in *E. coli*. Some constructs were expressed in CEF (chicken embryo fibroblasts, data not shown). Some constructs include one or more influenza gene segment(s) (e.g. HA, NA, NP, Hat, Some constructs include native or IRES or non-IRES constructs. Other constructs include native, C13L and IRES/C13L constructs with and without an pathogen associated gene segment.

Immunization and Challenge

Groups of mice (e.g Harlan Sprague Dawley, Indianapolis, Ind.) received primary and booster immunizations with each vaccine candidate via intramuscular injections into hind legs. Then the mice were challenges with various viruses disclosed herein for protection.

Serology

Serum samples were collected post-primary vaccination and post-boost (pre-challenge) by means known in the art to assess antibody titers against influenza or poxvirus.

Statistical Analysis

The Student's t-test and the Logrank test were used to compare groups of data. Probability values <0.05 were considered significant using the GraphPad Prism 5 software (La Jolla, Calif.) for all statistical analyses.

Possible Secretory Signal Sequences of Use for Constructs Herein

| VV-cop have SSP | IN MVA |
|---|---|
| A13L | |
| A14L | |
| A39R | |
| A41L | |
| A56R | yes |
| B19R | no |
| B25R | |
| B5R | |
| B7R | |
| B8R | no |
| B9R | |
| C11R | yes |
| C13L | no |
| C19L | no |
| C3L | |
| F5L | |
| G3L | |
| K2L | |
| M2L | no |

In certain experiments it was noted that IM vaccinations such as Prime/Boost scheme were very effective, that there was increased morbidity with prime only. An adjuvant may not be effective and that in certain experiments it was observed that there was an increase in morbidity & mortality with the flagellin. In other experiments, ID Vaccinations using all tested schemes provide complete protection with the least morbidity occurring with prime/boost. An adjuvant was not contributing and adjuvant alone does not provide protection.

Some dose ranges were tested in a mouse model for certain constructs disclosed herein. Some of the doses ranges were about $5\times10^5$ to about $5\times10^7$. Weight loss of test animals was one way to monitor effectiveness of vaccination formulations and constructs tested.

FIGS. 6A and 6B represent exemplary plots of parameters in mice after intramuscular (IM) introduction of various constructs of some embodiments described herein to the mice followed by challenge with influenza, A) Weight loss and B) Survival post-challenge.

FIGS. 7A and 7B represent exemplary plots of parameters in mice after intradermal (ID) introduction of various constructs of some embodiments described herein to the mice followed by challenge with influenza, A) Weight loss and B) Survival post-challenge/infection.

FIGS. 8A and 8B represent exemplary plots of parameters in mice after (A) intramuscular (IM) or (B) intradermal (ID) introduction of various constructs of some embodiments described herein to the mice followed by challenge with influenza. These exemplary experiments assess several clinical indications. The indications were graded in the mouse model on a scale of 0 to 4.0=no signs of illness, 1=ruffled fur; 2=pitted coat, hunched posture, shivering and slow movement; 3=labored breathing, anorexia, little/no movement and 4=paralysis, moribund.

FIG. 9 represents an exemplary plot that illustrates viral titers in lung after introduction of various constructs of some embodiments described herein to the mice followed by challenge with influenza. Mice were sacrificed in each group on day 4 (post challenge/infection, 3 mice per group) and lungs were homogenized and tittered on MDCKs. Log virus titer is presented.

Table 1 represents some of the MVA influenza transfer vectors and constructs generated and tested.

FIGS. 10A and 10B represent exemplary plots of percent weight change in mice after introduction of 2 different constructs of some embodiments described herein having the HA gene segment in each construct followed by challenge with influenza. These construct were administered at different doses ($5\times10^5$ to $5\times10^7$)

FIGS. 11A and 11B represent exemplary plots of percent weight change in mice after introduction of 2 different constructs of some embodiments described herein followed by challenge with influenza. In A), these construct were administered at different doses (5×105 to 5×107). In B. a traceable compound was linked to an MVA construct.

FIGS. 12A and 12B represent exemplary plots of percent weight change in mice after introduction of 2 different constructs at various concentrations of some embodiments described herein followed by challenge with influenza. These construct were administered at different doses (5×105 to 5×107).

FIGS. 13A and 13B represent exemplary plots of percent survival in mice after introduction of 2 different constructs at various concentrations of some embodiments described herein followed by challenge with influenza. These construct were administered at different doses (5×105 to 5×107). Some of the constructs included additional elements, tPA and IRES. It was observed at day 8 that mice having constructs with an IRES and tPA element had decreased survival than MVA/HA alone in a construct.

FIGS. 14A and 14B represent exemplary plots of survival in mice after introduction of 2 different constructs at various concentrations of some embodiments described herein followed by challenge with influenza. These construct were administered at different doses (5×105 to 5×107). Some of the constructs included additional elements, tPA and IRES sequences (A). It was observed at day 8 that mice having constructs with an IRES and tpa element had decreased survival than MVA/HA alone in a construct. When the tPA element was replaced with another secretory signal C13L, survival was 100 percent for the time period tested.

FIGS. 15A and 15B represent exemplary plots of survival in mice after introduction of 2 different constructs at various concentrations of some embodiments described herein followed by challenge with influenza (dpi represents days post infection). These construct were administered at different doses (5×105 to 5×107).

Figure 16A:
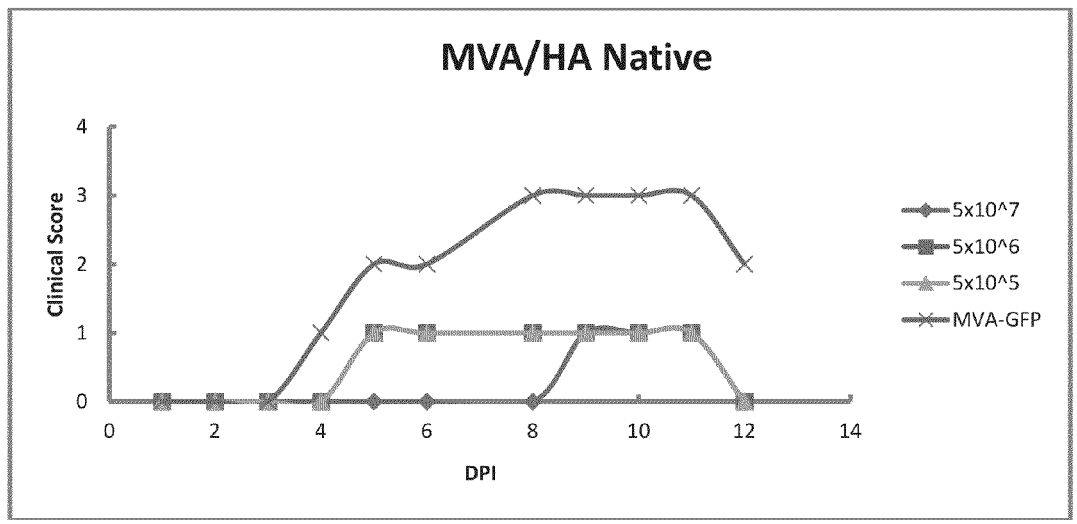
FIGS. 16A and 16B represent exemplary plots of clinical scores (e.g. physical and physiological parameters) in mice after introduction of 2 different constructs at various concentrations of some embodiments described herein followed by challenge with influenza.
Figure 16B:
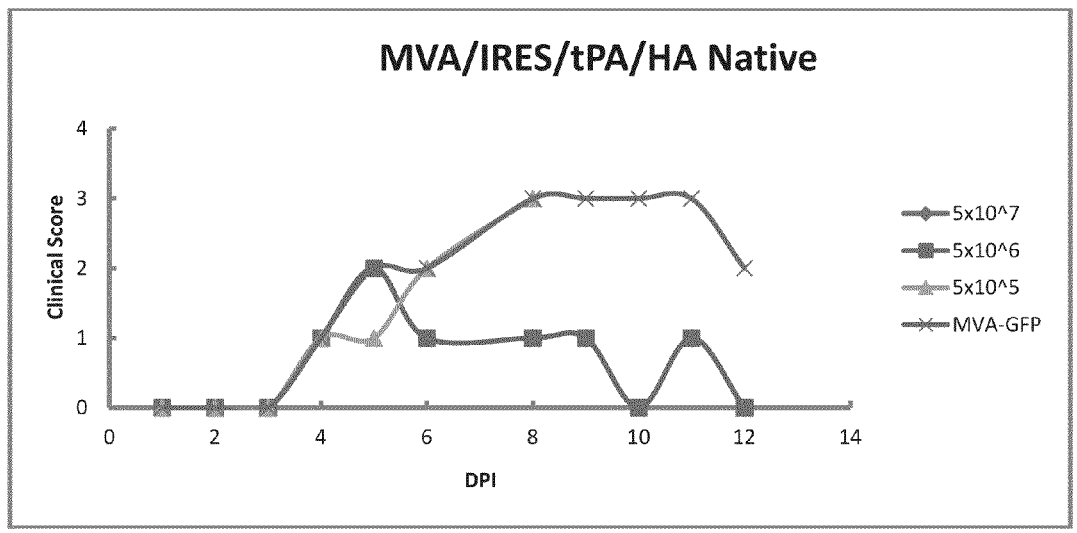

FIGS. 16A and 16B represent exemplary plots of clinical scores (e.g. physical and physiological parameters, see above scores from 0 to 4) in mice after introduction of 2 different constructs at various concentrations of some embodiments described herein followed by challenge with influenza. These construct were administered at different doses (5×105 to 5×107). In addition an MVA construct linked to a detectible marker was also introduced and followed in the mice.

Figures 17A, 17B:
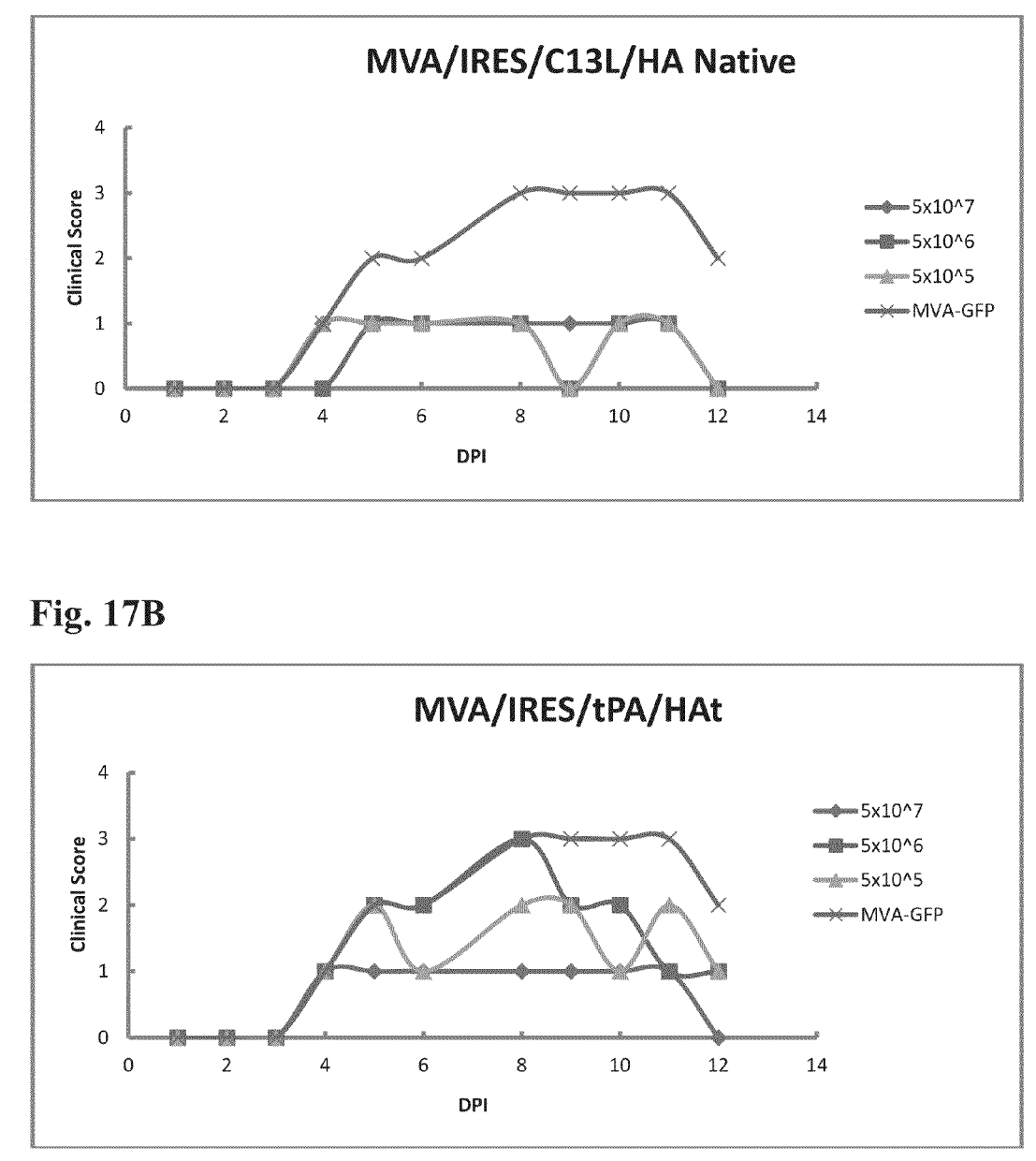

FIGS. 17A and 17B represent exemplary plots of clinical scores (e.g. physical and physiological parameters) in mice after introduction of 2 different constructs at various concentrations of some embodiments described herein followed by challenge with influenza. These construct were administered at different doses (5×105 to 5×107). In addition an MVA construct linked to a detectible marker (GFP) was also introduced and followed in the mice.

Figure 18:
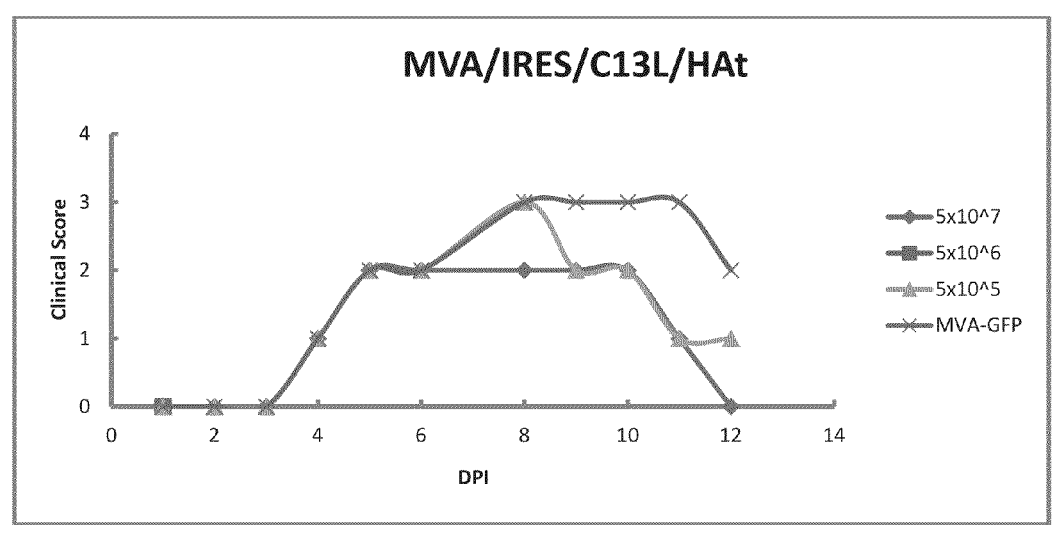

FIG. 18 represents an exemplary plot of clinical scores (e.g. physical and physiological parameters) in mice after introduction of a construct at various concentrations of some embodiments described herein followed by challenge with influenza. These construct were administered at different doses (5×105 to 5×107). In addition an MVA construct linked to a detectible marker (GFP) was also introduced and followed in the mice.

Example 6

Groups of mice (n=8) were inoculated intradermally with modified vaccinia Ankara (MVA) three month prior to intradermal vaccination with MVA/flu vaccines expressing hemagglutinin and/or nucleoprotein in with or without secretory signal (C13L).

Table 2: represents Antibody titers (Geometric mean titer—GMT) of serum samples following prime and booster (intradermal) vaccination with MVA/influenza vaccines in mice with pre-existing immunity to vaccinia:

| Vaccine Construct | Sampling | |
|---|---|---|
| | Pre-Boost | Post-Boost |
| MVA/HA | $3.61^c$ | $697.92^a$ |
| MVA/C13L/HA | $1.00^c$ | $65.42^b$ |
| MVA/C13L/NP | $1.00^c$ | $1.00^c$ |
| MVA/HA/C13L/NP | $2.11^c$ | $697.92^a$ |
| MVA/GFP | $1.00^c$ | $1.00^c$ |

Figure 19A:
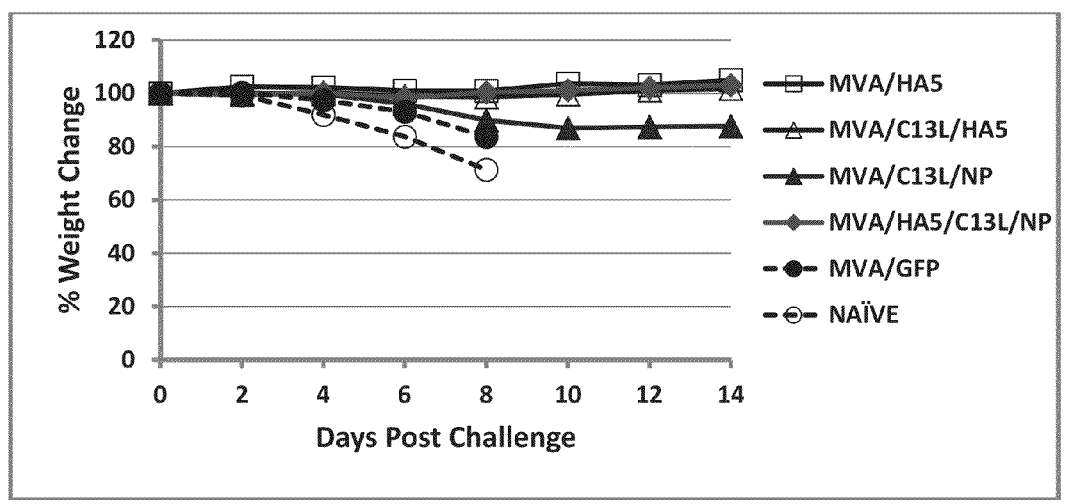
FIGS. 19A and 19B represent exemplary plots of percent weight change (FIG. 19A) and assessed clinical scores (FIG. 19B) in mice after introduction of different constructs in mice pre-exposed to vaccinia followed by challenge with influenza.
Figure 19B:
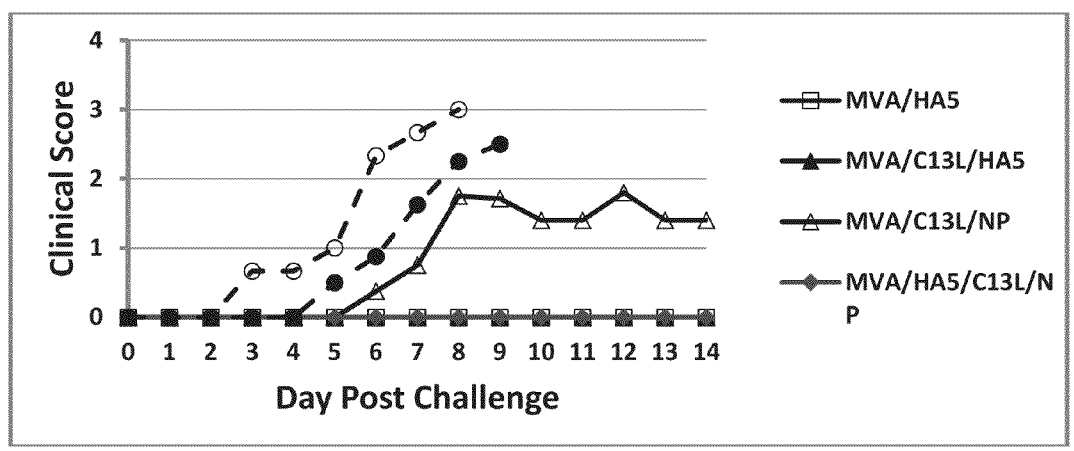
Figure 20:
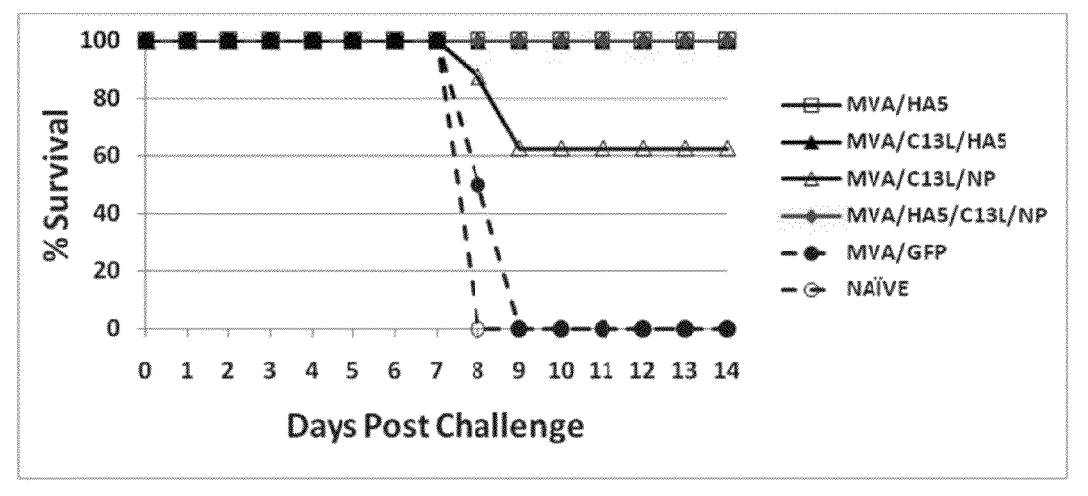

$^{a\text{-}c}$groups with different letters differ significantly ($P < 0.05$) by ANOVA FIGS. 19A and 19B represent (A) mean weigh changes in immunized mice challenged with Influenza A/Vietnam/1203-H5N1 virus ($10^4$ $TCID_{50}$) 4 wks post-booster vaccination with MVA/Flu vaccines. Mice had pre-existing immunity to vaccinia. Mice immunized with MVA/Flu containing the hemagglutinin antigen did not lose weight; and (B) represents Clinical score of mice challenged with Influenza A/Vietnam/1203-H5N1 virus ($10^4$ $TCID_{50}$) 4 wks post-booster vaccination with MVA/Flu vaccines. Mice had pre-existing immunity to vaccinia prior to immunization of MVA/Flu vaccines. Clinical scores 0-4 are detailed above FIG. 20 represents survival rates of immunized mice (using the same constructs as in FIGS. 19A and B above) challenged with Influenza A/Vietnam/1203-H5N1 virus (104 TCID50) 4 wks post-booster vaccination with MVA/Flu vaccines. Mice had pre-existing immunity to vaccinia prior to immunization of MVA/Flu vaccines. All mice immunized with MVA/Flu containing the hemagglutinin antigen survived challenge with lethal dose of Influenza A/Vietnam/1203-H5N1 virus.

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. An immunogenic pharmaceutical composition for administration to a subject comprising:
   one or more constructs, comprising:
   a modified or attenuated vaccinia virus construct encoding at least one vaccinia virus secretory signal sequence associated with at least one immunogenic non-vaccinia virus peptide
   wherein the at least one vaccinia virus secretory signal sequence comprises, at least one of a secretory signal sequence of C13L or B8R, and a pharmaceutically acceptable excipient, wherein the one or more peptides are capable of inducing an immune response in the subject.

2. The immunogenic composition of claim 1, wherein the non-vaccinia virus peptide is derived from bacteria, virus, mammals, fungi, protozoan, non-pathogenic organisms or a combination thereof.

3. The immunogenic composition of claim 1, wherein the non-vaccinia virus peptide comprises an influenza protein.

4. The immunogenic composition of claim 3, wherein the influenza protein comprises hemagglutinin (HA), neuraminidase (N), nucleoprotein (NP), matrix (M) or a combination thereof.

5. The immunogenic composition of claim 1, wherein the construct is a modified vaccinia Ankara (MVA) virus.

6. The immunogenic composition of claim 1, further comprising one or more translational control sequences.

7. A method for inducing an immune response in a subject comprising:

administering the immunogenic composition of claim 1 to the subject in an amount sufficient to induce an immune response in the subject.

8. The method of claim 7, wherein the modified vaccinia virus is a modified vaccinia Ankara (MVA).

9. A method for inducing an immune response in a subject comprising:

administering the immunogenic composition of claim 1 as a first composition to the subject in an amount sufficient to induce an immune response, followed by administering a second composition to the subject, the second composition comprising: a modified or attenuated vaccinia virus construct encoding one or more poxvirus constructs, comprising, at least one poxvirus secretory signal sequence and at least one non-poxvirus peptide, wherein the composition is capable of inducing an immune response in the subject when administered in an amount sufficient to induce an immune response.

10. The method of claim 9, wherein the vaccinia virus in the first composition is a modified vaccinia Ankara (MVA).

11. The method of claim 9, wherein the non-poxvirus peptide is derived from bacteria, virus, mammals, fungi, protozoan, non-pathogenic organisms or a combination thereof.

12. The method of claim 9, wherein the first composition is administered to the subject 6 months or less prior to the second composition.

13. A method for inducing an immune response in a subject previously exposed to poxvirus comprising:
   administering as a pre-boost dosage, the immunogenic composition of claim 1 to the subject in an amount sufficient to induce an immune response,
   wherein the vaccinia virus is a modified vaccinia Ankara (MVA).

14. The method of claim 13, further comprising administering a booster dosage of the immunogenic composition 6 months or less after administration of the pre-boost dosage of the immunogenic composition.

15. The method of claim 13, wherein administration of the immunogenic composition comprises intradermal administration.

16. A kit comprising;
   the immunogenic composition of claim 1; and at least one container.

17. The kit of claim 16, wherein at least one of the non-vaccinia virus peptides comprises one or more influenza virus protein(s).

18. A pharmaceutical composition for administration to a subject comprising:
   one or more constructs, comprising: a modified or attenuated vaccinia virus construct encoding at least one vaccinia virus secretory signal sequence associated with at least one non-vaccinia virus peptide, wherein the at least one vaccinia virus secretory signal sequence is a secretory signal of C13L, and
   a pharmaceutically acceptable excipient, wherein the one or more peptides are capable of inducing an immune response in the subject.

19. The pharmaceutical composition of claim 18, wherein the secretory signal sequence from C13L is the amino acid sequence represented by SEQ ID NO:1.

* * * * *

UNITED STATES PATENT AND TRADEMARK OFFICE
CERTIFICATE OF CORRECTION

| | |
|---|---|
| PATENT NO. | : 9,011,874 B2 |
| APPLICATION NO. | : 13/510601 |
| DATED | : April 21, 2015 |
| INVENTOR(S) | : Dan T. Stinchcomb et al. |

It is certified that error appears in the above-identified patent and that said Letters Patent is hereby corrected as shown below:

In the Specification:

Replace paragraph [0002] of the application as filed under FEDERALLY FUNDED RESEARCH with the corrected paragraph below:

"This invention was made with Government support under R43 AI061940 and R41 AI074308 awarded by the National Institutes of Health. The Government has certain rights in this invention."

Signed and Sealed this
Twenty-eighth Day of July, 2015

Michelle K. Lee
*Director of the United States Patent and Trademark Office*